US007427594B1

(12) United States Patent
Yu

(10) Patent No.: US 7,427,594 B1
(45) Date of Patent: Sep. 23, 2008

(54) METHODS AND PHARMACEUTICALS COMPOSITIONS FOR TREATING CORONARY ARTERY DISEASE, ISCHEMIA, AND VASCULAR DISEASE USING ANGIOPOIETINS

(75) Inventor: Qin Yu, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/375,765

(22) Filed: Feb. 26, 2003

Related U.S. Application Data

(60) Provisional application No. 60/359,679, filed on Feb. 26, 2002.

(51) Int. Cl.
*A61K 38/18* (2006.01)
*C07K 14/515* (2006.01)

(52) U.S. Cl. .................................. 514/12; 530/324
(58) Field of Classification Search .................. 514/2, 514/8; 530/300, 350
See application file for complete search history.

(56) References Cited

U.S. PATENT DOCUMENTS 6,916,637 B2 * 7/2005 Rieping et al. .............. 435/106

FOREIGN PATENT DOCUMENTS

WO WO 96/31598 * 10/1996

OTHER PUBLICATIONS

Hattori et al. Vascular endothelial growth factor and angiopoietin-1 stimulate postnatal hematopoiesis by recruitment of vasculogenic and hematopoietic stem cells. J. Exp. Med. 193:1005-1014, 2001.*
Rudinger, J. Characteristics of the amino acids as components of a peptide hormone sequence. In: Peptide hormones (Parsons, JA, ed.), University Park Press, Baltimore, pp. 1-7, 1976.*
Ngo et al. Computational complexity, protein structure prediction and the Levinthal Paradox. In: The protein folding problem and tertiary structure prediction (Merz et al., eds.), Birkhauser, Boston, pp. 1-491-495, 1994.*
Koblizek et al., Current Biology, 8:529-432, 1998.*
Asahara, Takayuki, et al. "Tie2 Receptor Ligands, Angiopoietin-1 and Angiopoietin-2, Modulate VEGF-induced Postnatal Neovascularization" Circulation Res. (1998) 83:233-240.
Davis, Samuel, et al. "Isolation of Angiopoietin-1, A Ligand for the Tie2 Receptor, by Secretion-Trap Expression Cloning", Cell (1996) 87:1161-1169.
Dumont, Daniel J., et al. "Dominant-Negative and Targeted Null Mutations in the Endothelial Receptor Tyrosine Kinase, TEK, Reveal a Critical Role in Vasculogenesis of the Embryo" Genes & Development (1994) 8:1897-1909.
Fidler, Isaiah J., et al. "The Implications of Angiogenesis for the Biology and Therapy of Cancer Metastasis" Cell. (1994) 79:185-188.

Fong, Guo-Hua., et al. "Role of the FLT-1 Receptor Tyrosine Kinase in Regulating the Assembly of Vascular Endothelium" Nature (1995) 376:66-70.
Gale, Nicolas W., "Growth Factors Acting via Endothelial Cell-Specific Receptor Tyrosine Kinases: VEGF's Angiopoietins, and Ephrins in Vascular Development" Genes&Development (1999) 13:1055-1066.
Hanahan, Douglas, et al. "Patterns and Emerging Mechanisms of the Angiogenic Switch During Tumorigenesis" Cell (1996) 86:353-364.
Hanahan, Douglas, et al, "Signaling Vascular Morphogenesis and Maintenance" Science (1997) 277:48-50.
Hayes, Andrew J., et al. "Angiopoietin-1 and its Receptor Tie-2 Participate in the Regulation of Capillary-Like Tubule Formation and Survival of Endothelial Cells" Microvascular Research. (1999) 58:244-237.
Holash, J., et al. "New Model of Tumor Angiogenesis: Dymanic Balance Between Vessel Regression and Growth Mediated by Angiopoietins and VEGF" Oncogene. (1999) 18: 5356-5362.
Holash, J., et al. "Vessel Cooption, Regression, and Growth in Tumors Mediated by Angiopoietins and VEGF" Science. (1999) 284:1994-1998.
Holmgren, Lars, et al. "Dormancy of Micrometastases: Balanced Proliferation and Apoptosis in the Presence of Angiogenesis Suppression" Nature Medicine. (1995) 2: 149-153.
Ingber, Donald E., et al. "How Does Extracellular Matrix Control Capillary Morphogenesis?" Cell (1989) 58:803-805.
Kim, Injune, et al. "Angiopoietin-1 Regulates Endothelial Cell Survival Through the Phosphatidylinositol 3'-KINASE/AKT Signal Transduction Pathway" Circ Res. (2000) 86:24-29.
Kim, Injune, et al. "Tumor Necrosis Factor-α Upregulates Angiopoietin-2 in Human Umbilical Vein Endothelial Cells" Biochemical and Biophysical Research Communications. (2000) 269:361-365.

(Continued)

*Primary Examiner*—Marianne P Allen
(74) *Attorney, Agent, or Firm*—Pepper Hamilton LLP

(57) ABSTRACT

Pharmaceutical compositions that comprise a pharmaceutically acceptable carrier and either a therapeutically effective amount of an ECM-binding fragment of Ang-1 protein that comprises SEQ ID NO:1 and/or SEQ ID NO:2 or a homologous peptide thereof and pharmaceutical compositions that comprise a pharmaceutically acceptable carrier and a vector comprising a nucleic acid molecule that comprises the nucleotide sequence that encodes an ECM-binding fragment of Ang-1 protein that comprises SEQ ID NO:1 and/or SEQ ID NO:2 or a homologous peptide thereof are disclosed. Methods of using such compositions to treat individuals suspected of having coronary artery disease, vascular disease or a condition involving ischemia and to promote angiogenesis, endothelial survival and maintaining vascular integrity are disclosed. Methods to identify compounds that modulates binding of Ang-1 to ECM are disclosed. Pharmaceutical compositions which comprise a therapeutically effective amount of Ang-2 protein and/or a vector comprising a nucleic acid molecule that comprises the nucleotide coding sequence of Ang-2 and methods of using such compositions to treat individuals suspected of having cancer are disclosed.

11 Claims, 9 Drawing Sheets

OTHER PUBLICATIONS

Kim, Jin K., et al. "Inhibtion of Vascular Endothelial Growth Factor-Induced Angiogenesis Suppresses Tumour Growth In Vivo" Nature (1993) 362:841-844.

Klagsbrun, Michael "Mediators of Angiogenesis: The Biological Significance of Basic Fibroblast Growth Factor (bFGF)-Heparin and Heparan Sulfate Interactions" Cancer Biology. (1992) 3:81-87.

Koblizek Thomas I., et al. "Angiopoietin-1 Induces Sprouting Angiogenesis In Vitro" Current Biology (1998) 8:529-532.

Kuno, Kouji, et al. "Adamts-1 Protein Anchors at the Extracellular Matrix Through the Thrombospondin Type I Motifs and its Spacing Region" The Journal of Biological Chemistry. (1998) 273:13912-13917.

Kwak, Hee Jin, et al. "Angiopoietin-1 Inhibits Irradiation- and Mannitol-Tnduced Apoptosis in Endothelial Cells" Circulation (2000) 101:2317-2324.

Lauren, Juha, et al. Is Angiopoietin-2 Necessary for the Initiation of Tumor Angiogenesis? American Journal of Pathology. (1998) 153:1333-1339.

Maisonpierre, Peter C., et al. "Angiopoietin-2, A Natural Antagonists for Tie2 That Disrupts in Vivo Angiogenesis" Science (1997) 277:55-60.

Mandriota, Stefano, et al. "Regulation of Angiopoietin-2 mRNA Levels in Bovine Microvascular Endothelial Cells by Cytokines and Hypoxia" Circulation Res. (1998) 83: 852-859.

Massague, Joan "The Transforming Growth Factor-β Family" Annu. Rev. Cell Biol. (1990) 6:597-641.

Millauer, Birgit, et al. "Glioblastoma Growth Inhibited in Vivo by a Dominant-Negative FLK-1 Mutant" Nature (1994) 367:576-579.

Mustonen Tuija, et al. "Endothelial Receptor Tyrosine Kinases Involved in Angiogenesis" The Journal of Cell Biology (1995) 129:895-898.

O'Reilly Michael S., et al. "Angiostatin: A Novel Angiogenesis Inhibitor That Mediates the Suppression of Metastases by a Lewis Lung Carcinoma" Cell. (1994) 79:315-328.

Oh, Hideyasu, et al. "Hypoxia and Vascular Endothelial Growth Factor Selectively Up-Regulate Angiopoietin-2 in Bovine Microvascular Endothelial Cells" The Journal of Biological Chemistry. (1999) 274:15732-15739.

Ortega, Nathalie, et al. "Control of Vascular Endothelial Growth Factor Angiogenic Activity by the Extracellular Matrix" Biology of the Cell. (1998) 90:381-390.

Papapetropoulos, Andreas, et al. "Angiopoietin-1 Inhibits Endothelial Cell Apoptosis via the Akt/Survivin Pathway" The journal of Biological Chemistry. (2000) 275:9102-9105.

Procopio, William N., et al. "Angiopoietin-1 and -2 Coiled Coil Domains Mediate Distinct Homo-Oligomerization Patterns, but Fibrinogen-Like Domains Mediate Ligand Activity" The Journal of Biological Chemistry (1999) 274:30196-30201.

Risau, Werner, et al. "Mechanisms of Angiogenesis" Nature (1997) 386:671-674.

Sato, Thomas N., et al. "Distinct Roles of the Receptor Tyrosine Kinases Tie-1 and Tie-2 in Blood Vessel Formation" Nature (1995) 376:70-74.

Sherwood, Louis M., et al. "Tumor Angiogenesis: Therapeutic Implications" The New England Journal of Medicine (1971) 285:1182-1186.

Stratmann, Astrid, et al. "Cell Type-Specific Expression of Angiopoietin-1 and Angiopoietin-2 Suggests a Role in Glioblastoma Angiogenesis" (1998) 153:1459-1466.

Suri, Chitra, et al. "Increased Vascularization in Mice Overexpressing Angiopoietin-1" Science (1998) 282:468-471.

Suri, Chitra, et al. "Requisite Role of Angiopoietin-1, A Ligand for the Tie2 Receptor During Embryonic Angiogenesis" Cell (1996) 87:1171-1180.

Thurston, G., et al. "Leakage-Resistant Blood Vessels in Mice Transgenically Overexpressing Angiopoietin-1" Science (1999) 286:2611-2514.

Thurston, Gavin, et al. "Angiopoietin-1 Protects the Adult Vasculature Against Plasma Leakage" *Nature Medicine* (2000) 6:460-463.

Valenzuela, David M., et al. "Angiopoietins 3 and 4: Diverging Gene Counterparts in Mice and Humans" Proc. Natl. Acad. Sci. USA (1999) 96:1904-1909.

Witzenbichler, Bernhard, et al. "Chemotactic Properties of Angiopoietin-1 and -2, Ligands for the Endothelial-Specific Receptor Tyrosine Kinase Tie-2" The Journal of Biological Chemistry (1998) 273:18514-18521.

Xu, Yin et al. "Angiopoietin-1, Unlike Angiopoietin-2, is Incorporated Into the Extracellular Matrix via its Linker Peptide Region" The Journal of Biological Chemistry. (2001) 276:3490-34998.

Yancopoulos, George D., et al. "Vascular-Specific Growth Factors and Blood Vessel Formation" Nature (2000) 407:242-248.

Yeo, Tet-Kin, et al. "Increased Hyaluronan at Sites of Attachment to Mesentery by CD44-Positive Mouse Ovarian and Breast Tumor Cells" American Journal of Pathology. (1996) 148:1733-1740.

Yu, Qin, et al. "Angiopoietin-2 is Implicated in the Regulation of Tumor Angiogenesis" American Journal of Pathology (2001) 158:563-570.

Yu, Qin, et al. "Localization of Matrix Metalloproteinase 9 to the Cell Surface Provides a Mechanism for CD-44-Mediated Tumor Invasion" Genes & Development. (1999) 13:35-48.

\* cited by examiner

SEQUENCE LISTING

```
<160> NUMBER OF SEQ ID NOS: 19

<210> SEQ ID NO 1
<211> LENGTH: 26
<212> TYPE: PRT
<213> ORGANISM: Mus musculus

<400> SEQUENCE: 1

Val His Asn Leu Val Ser Leu Cys Thr Lys Glu Gly Val Leu Leu Lys
1               5                   10                  15

Gly Gly Lys Arg Glu Glu Glu Lys Pro Phe
            20                  25

<210> SEQ ID NO 2
<211> LENGTH: 26
<212> TYPE: PRT
<213> ORGANISM: homo sapiens

<400> SEQUENCE: 2

Val His Asn Leu Val Asn Leu Cys Thr Lys Glu Gly Val Leu Leu Lys
1               5                   10                  15

Gly Gly Lys Arg Glu Glu Glu Lys Pro Phe
            20                  25

<210> SEQ ID NO 3
<211> LENGTH: 2149
<212> TYPE: DNA
<213> ORGANISM: Homo sapiens
```

<400> SEQUENCE: 3

```
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aattttagaa caaagctaac aaatggctag ttttctatga ttcttcttca     180
aacgctttct ttgagggga aagagtcaaa caaacaagca gttttacctg aaataaagaa      240
ctagttttag aggtcagaag aaaggagcaa gttttgcgag aggcacggaa ggagtgtgct     300
ggcagtacaa tgacagtttt cctttccttt gctttcctcg ctgccattct gactcacata     360
gggtgcagca atcagcgccg aagtccagaa acagtggga gaagatataa ccggattcaa      420
catgggcaat gtgcctacac tttcattctt ccagaacacg atggcaactg tcgtgagagt     480
acgacagacc agtacaacac aaacgctctg cagagagatg ctccacacgt ggaaccggat     540
ttctcttccc agaaacttca acatctgaaa catgtgatgg aaaattatac tcagtggctg     600
caaaaacttg agaattacat tgtggaaaac atgaagtcgg agatggccca gatacagcag     660
aatgcagttc agaaccacac ggctaccatg ctggagatag aaccagcct cctctctcag      720
actgcagagc agaccagaaa gctgacagat gttgagaccc aggtactaaa tcaaacttct     780
cgacttgaga tacagctgct ggagaattca ttatccacct acaagctaga gaagcaactt     840
cttcaacaga caaatgaaat cttgaagatc catgaaaaaa acagtttatt agaacataaa     900
atcttagaaa tggaaggaaa acacaaggaa gagttggaca ccttaaagga agagaaagag     960
aaccttcaag gcttggttac tcgtcaaaca tatataatcc aggagctgga aaagcaatta    1020
aacagagcta ccaccaacaa cagtgtcctt cagaagcagc aactggagct gatggacaca    1080
gtccacaacc ttgtcaatct ttgcactaaa gaaggtgttt tactaaaggg aggaaaaaga    1140
gaggaagaga aaccatttag agactgtgca gatgtatatc aagctggttt taataaaagt    1200
ggaatctaca ctatttatat taataatatg ccagaaccca aaaaggtgtt ttgcaatatg    1260
gatgtcaatg ggggaggttg gactgtaata caacatcgtg aagatggaag tctagatttc    1320
caaagaggct ggaaggaata taaaatgggt tttggaaatc cctccggtga atattggctg    1380
gggaatgagt ttatttttgc cattaccagt cagaggcagt acatgctaag aattgagtta    1440
atggactggg aagggaaccg agcctattca cagtatgaca gattccacat aggaaatgaa    1500
aagcaaaact ataggttgta tttaaaaggt cacactggga cagcaggaaa acagagcagc    1560
ctgatcttac acgtgctga tttcagcact aaagatgctg ataatgacaa ctgtatgtgc    1620
aaatgtgccc tcatgttaac aggaggatgg tggtttgatg cttgtggccc ctccaatcta    1680
aatgaatgt tctatactgc gggacaaaac catggaaaac tgaatgggat aaagtggcac    1740
tacttcaaag ggcccagtta ctccttacgt tccacaacta tgatgattcg accttagat    1800
ttttgaaagc gcaatgtcag aagcgattat gaaagcaaca aagaaatccg agaagctgc    1860
caggtgagaa actgtttgaa aacttcagaa gcaaacaata ttgtctccct tccagcaata    1920
agtggtagtt atgtgaagtc accaaggttc ttgaccgtga atctggagcc gtttgagttc    1980
acaagagtct ctacttgggg tgacagtgct cacgtggctc gactatagaa aactccactg    2040
actgtcgggc tttaaaaagg gaagaaactg ctgagcttgc tgtgcttcaa actactactg    2100
gaccttattt tggaactatg gtagccagat gataaatatg gttaatttc                2149
```

<210> SEQ ID NO 4
<211> LENGTH: 498
<212> TYPE: PRT

<213> ORGANISM: Homo sapiens

<400> SEQUENCE: 4

```
Met Thr Val Phe Leu Ser Phe Ala Phe Leu Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Thr Thr Asp Gln Tyr Asn Thr
        50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270

Lys Gly Gly Lys Arg Glu Glu Lys Pro Phe Arg Asp Cys Ala Asp
        275                 280                 285

Val Tyr Gln Ala Gly Phe Asn Lys Ser Gly Ile Tyr Thr Ile Tyr Ile
290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
370                 375                 380

Ala Tyr Ser Gln Tyr Asp Arg Phe His Ile Gly Asn Glu Lys Gln Asn
385                 390                 395                 400
```

```
Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
        435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 5
<211> LENGTH: 2044
<212> TYPE: DNA
<213> ORGANISM: Mus musculus

<400> SEQUENCE: 5
```

| | | | | | |
|---|---|---|---|---|---|
| ctgacgcggg | caggctccac | gctgaacggt | tacacagaga | ggaaacaata | aatctaagct | 60 |
| actattgcaa | taaatatctc | aagttttaac | gaaggaaact | atcattacag | ttaaaatttt | 120 |
| ttaaagtaac | gcttttttag | aacaaagcta | acaaatggct | agttttctgt | ggatcttctt | 180 |
| caaacgcttt | ctttaacggg | gaaagagtca | acaagcagt | tttacctgaa | ataaagaact | 240 |
| agtttaaagg | tcagaagaga | agagcaagct | ttgcaggagg | cacggaaggc | aagcgctggc | 300 |
| agtacaatga | cagttttcct | ttcctttgca | ttcttcgctg | ccattctgac | tcacataggg | 360 |
| tgcagcaacc | agcgccgaaa | tccagaaaac | ggagggagaa | gatataaccg | gattcaacat | 420 |
| gggcaatgtg | cctacacttt | cattcttcca | gaacacgacg | ggaactgccg | tgagagtgcg | 480 |
| acagagcagt | acaacaccaa | cgctctgcaa | agggatgctc | cacacgtgga | gccggatttc | 540 |
| tcttcccaga | aacttcagca | tctggagcat | gtgatggaaa | attatactca | gtggctgcaa | 600 |
| aaacttgaga | attacattgt | ggaaaatatg | aagtcggaga | tggcccagat | acaacagaat | 660 |
| gctgttcaaa | accacacggc | caccatgctt | gagataggaa | ccagtctctt | atctcagact | 720 |
| gcagagcaga | cccgaaagct | gacagatgtt | gagacccagg | tactaaatca | acatcccga | 780 |
| cttgaaatac | aactgctaga | gaattcatta | tcaacataca | agctagagaa | gcaacttctc | 840 |
| caacagacaa | atgaaattct | gaagattcac | gaaaaaaaca | gtttactaga | gcacaaaatc | 900 |
| ttagaaatgg | agggaaaaca | caaagaagaa | ttggacacct | tgaaggagga | gaaagaaaac | 960 |
| cttcaaggct | tggtttctcg | tcagacattc | atcatccagg | agttggagaa | gcaacttagt | 1020 |
| agagctacca | acaacaacag | catcctgcag | aagcaacaac | tggagctcat | ggacacagtt | 1080 |
| cataaccttg | tcagcctttg | cactaaagaa | ggtgttttgc | taagggagg | aaaaagagaa | 1140 |
| gaagagaaac | catttcgaga | ctgtgcagat | gtatatcaag | ctggttttaa | taaaagtgga | 1200 |
| atctacacta | tttattttaa | taatatgcca | gaacccaaaa | aggtattttg | caatatggat | 1260 |
| gtgaatgggg | gaggttggac | agtaatacaa | caccgggaag | atggaagcct | ggatttccag | 1320 |
| aggggctgga | aggagtataa | aatgggtttt | gggaatccct | ctggtgaata | ttggctcggg | 1380 |
| aacgagttca | ttttttgcaat | aaccagtcag | aggcagtaca | tgctgaggat | tgagctgatg | 1440 |
| gactgggaag | ggaaccgagc | ctactcacag | tacgacagat | tccacatagg | aaatgaaaag | 1500 |
| cagaactata | ggttatattt | aaaaggtcac | acagggacag | caggcaaaca | gagcagcttg | 1560 |

-continued

```
atcttacacg gtgctgattt cagcacgaag gatgctgata acgacaactg tatgtgcaaa   1620
tgcgctctca tgctaacagg aggttggtgg ttcgatgcct gtggcccttc caatctaaat   1680
ggaatgttct acactgcggg acaaaatcat ggaaaactga atgggataaa gtggcactac   1740
ttcaaagggc ccagttactc cttacgttcc accaccatga tgatccggcc cttggacttt   1800
tgaaggtgct atgccagtat tagaaagctg caaagaaagc tgggcatgtt cccagatgag   1860
aagctagtca gaggcttcag aaacaaccaa cattgtctcc gttccagcag caagtggtta   1920
tgtcatgtca cctgggtact taacaatgga tttggagcct tctgaggtca acagaatcgc   1980
cacttgggtc cagagaatgc cactcacaat catgtttaaa agggaagaaa cttctcagct   2040
tgct                                                                 2044
```

<210> SEQ ID NO 6
<211> LENGTH: 498
<212> TYPE: PRT
<213> ORGANISM: Mus musculus

<400> SEQUENCE: 6

| | | | | | | | | | | | | | | |
|---|---|---|---|---|---|---|---|---|---|---|---|---|---|---|
| Met | Thr | Val | Phe | Leu | Ser | Phe | Ala | Phe | Phe | Ala | Ala | Ile | Leu | Thr | His |
| 1 | | | | 5 | | | | | 10 | | | | | 15 | |

Ile Gly Cys Ser Asn Gln Arg Arg Asn Pro Glu Asn Gly Gly Arg Arg
         20                  25                  30

Tyr Asn Arg Ile Gln His Gly Gln Cys Ala Tyr Thr Phe Ile Leu Pro
             35                  40                  45

Glu His Asp Gly Asn Cys Arg Glu Ser Ala Thr Glu Gln Tyr Asn Thr
 50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Ser
    210                 215                 220

Arg Gln Thr Phe Ile Ile Gln Glu Leu Glu Lys Gln Leu Ser Arg Ala
225                 230                 235                 240

Thr Asn Asn Asn Ser Ile Leu Gln Lys Gln Gln Leu Glu Leu Met Asp
                245                 250                 255

Thr Val His Asn Leu Val Ser Leu Cys Thr Lys Glu Gly Val Leu Leu
            260                 265                 270

Lys Gly Gly Lys Arg Glu Glu Glu Lys Pro Phe Arg Asp Cys Ala Asp

-continued

```
                275                 280                 285
Val Tyr Gln Ala Gly Phe Asn Lys Ser Gly Ile Tyr Thr Ile Tyr Phe
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
            355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
        435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 7
<211> LENGTH: 1891
<212> TYPE: DNA
<213> ORGANISM: Rattus norvegicus

<400> SEQUENCE: 7
aggctccacg ctgaacggtt acacagagag gaaacaataa atctaagcta ctattgcaat       60
aaatatctca agttttaacg aaggaaacta tcattacagt aattttttta agtaacgcgt      120
tttataacaa agctaacaaa tggctagttt tctgtggatc ttcttcaaat gctttcttta      180
acggggagag cgtcaaacaa ccagttttac ctgaaataaa gaactagttt aaaggtcaga      240
agagaggagc aagctttgca ggaggcacgg aaggcgagtg ctggcagtac aatgacagtt      300
ttcctttcct ttgcattctt cgctgccatt ctgactcaca tagggtgcag caaccagcgc      360
cggagtccag aaaacggagg gagaagatat aaccgaattc aacatgggca atgtgcctac      420
actttcattc ttccagaaca cgacgggaac tgccgtgaga gtgcgacaga gcagtacaac      480
accaacgctc tgcaagggga tgctccacac gtggagacgg atttctcttc ccagaaactt      540
cagcatctgg agcatgtgat ggaaaattat actcagtggc tgcaaaaact tgagaattac      600
attgtggaaa atatgaagtc ggagatggcc cagatacaac agaatgcggt tcaaaaccac      660
acggccacca tgctggagat aggaaccagc ctcttgtctc agactgcaga gcagacccga      720
aagctcacag atgtgtggag accaggtact aatcaaacat cccgtcttga aatccaactg      780
ctggagaatt cattatcaac atacgagcta gagaacagc ttctccaaca gacaaatgaa      840
```

-continued

```
attctgaaga ttcaggaaaa aaacagttta ttagagcata aaatcctaga aatggaggga    900
aaacacaagg aagagctgga caccttgaag gaggagaaag aaaaccttca aggcttggtt    960
actcgtcaga cattcatcat ccaagaattg gagaagcaac ttagcagagc taccagcaac   1020
aacagtgttc tgcagaagca acaactggag ctcatggaca cagtccataa ccttgtcagc   1080
ctttgcacaa agaagttttt gctaaaggga ggaaaaagag aagaagagaa accatttcga   1140
gactgtgcag atgtatatca agctggtttt aataagagtg gaatctacac tatttatttt   1200
aataatatgc cagaacccaa aaaggtattt tgcaatatgg atgtgaatga aggaggatgg   1260
acagtaatac aacaccgtga ggatggaagc ctagatttcc agaggggctg gaaggagtat   1320
aaaatgggtt ttgggaatcc ctctggtgaa tattggcttg ggaacgagtt cattttttgca  1380
ataaccagtc agaggcagta catgctgagg atcgagctga tggactggga agggaaccga   1440
gcctactcac agtacgacag attccacata ggaaaccaga agcagaacta caggttatat   1500
ttaaagggtc acacggggac agcaggcaaa cagagcagct tgatcttaca tggtgctgat   1560
ttcagcacaa aggacgctga taacgacaac tgtatgtgca aatgcgccct tatgctaaca   1620
ggaggttggt ggtttgatgc ctgtggccct tccaatctaa acggaatgtt ctacactgca   1680
gggcaaaacc atggaaaact gaatgggata agtggcact acttcaaagg acccagttac    1740
tccttacgtt ccacaaccat gatgatccgg cccttggact tctgaaggcg ctatgcctag   1800
tattagaaac ctgaaataaa tctggggatg ttcccgaatg agaagctatc tggaagcttc   1860
cgaaacaacc cagcattgtc tccgttccag c                                  1891
```

<210> SEQ ID NO 8
<211> LENGTH: 497
<212> TYPE: PRT
<213> ORGANISM: Rattus norvegicus

<400> SEQUENCE: 8

```
Met Thr Val Phe Leu Ser Phe Ala Phe Phe Ala Ala Ile Leu Thr His
1               5                   10                  15

Ile Gly Cys Ser Asn Gln Arg Arg Ser Pro Glu Asn Gly Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Ala Thr Glu Gln Tyr Asn Thr
    50                  55                  60

Asn Ala Leu Gln Arg Asp Ala Pro His Val Thr Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Glu Leu Glu Lys Gln
                165                 170                 175

Leu Leu Gln Gln Thr Asn Glu Ile Leu Lys Ile Gln Glu Lys Asn Ser
            180                 185                 190
```

```
Leu Leu Glu His Lys Ile Leu Glu Met Glu Gly Lys His Lys Glu Glu
            195                 200                 205
Leu Asp Thr Leu Lys Glu Glu Lys Glu Asn Leu Gln Gly Leu Val Thr
            210                 215                 220
Arg Gln Thr Phe Ile Ile Gln Glu Leu Glu Lys Gln Leu Ser Arg Ala
225                 230                 235                 240
Thr Ser Asn Asn Ser Val Leu Gln Lys Gln Gln Leu Glu Leu Met Asp
                245                 250                 255
Thr Val His Asn Leu Val Ser Leu Cys Thr Lys Glu Val Leu Leu Lys
            260                 265                 270
Gly Gly Lys Arg Glu Glu Lys Pro Phe Arg Asp Cys Ala Asp Val
            275                 280                 285
Tyr Gln Ala Gly Phe Asn Lys Ser Gly Ile Tyr Thr Ile Tyr Phe Asn
            290                 295                 300
Asn Met Pro Glu Pro Lys Lys Val Phe Cys Asn Met Asp Val Asn Glu
305                 310                 315                 320
Gly Gly Trp Thr Val Ile Gln His Arg Glu Asp Gly Ser Leu Asp Phe
                325                 330                 335
Gln Arg Gly Trp Lys Glu Tyr Lys Met Gly Phe Gly Asn Pro Ser Gly
            340                 345                 350
Glu Tyr Trp Leu Gly Asn Glu Phe Ile Phe Ala Ile Thr Ser Gln Arg
            355                 360                 365
Gln Tyr Met Leu Arg Ile Glu Leu Met Asp Trp Glu Gly Asn Arg Ala
            370                 375                 380
Tyr Ser Gln Tyr Asp Arg Phe His Ile Gly Asn Gln Lys Gln Asn Tyr
385                 390                 395                 400
Arg Leu Tyr Leu Lys Gly His Thr Gly Thr Ala Gly Lys Gln Ser Ser
                405                 410                 415
Leu Ile Leu His Gly Ala Asp Phe Ser Thr Lys Asp Ala Asp Asn Asp
            420                 425                 430
Asn Cys Met Cys Lys Cys Ala Leu Met Leu Thr Gly Gly Trp Trp Phe
            435                 440                 445
Asp Ala Cys Gly Pro Ser Asn Leu Asn Gly Met Phe Tyr Thr Ala Gly
            450                 455                 460
Gln Asn His Gly Lys Leu Asn Gly Ile Lys Trp His Tyr Phe Lys Gly
465                 470                 475                 480
Pro Ser Tyr Ser Leu Arg Ser Thr Thr Met Met Ile Arg Pro Leu Asp
                485                 490                 495
Phe

<210> SEQ ID NO 9
<211> LENGTH: 2269
<212> TYPE: DNA
<213> ORGANISM: Homo sapiens

<400> SEQUENCE: 9
tgggttggtg tttatctcct cccagccttg agggagggaa caacactgta ggatctgggg      60
agagaggaac aaaggaccgt gaaagctgct ctgtaaaagc tgacacagcc ctcccaagtg     120
agcaggactg ttcttcccac tgcaatctga cagtttactg catgcctgga gagaacacag     180
cagtaaaaac caggtttgct actggaaaaa gaggaaagag aagactttca ttgacggacc     240
cagccatggc agcgtagcag ccctgcgttt cagacggcag cagctcggga ctctggacgt     300
gtgtttgccc tcaagtttgc taagctgctg gtttattact gaagaaagaa tgtggcagat     360
```

```
tgttttcttt actctgagct gtgatcttgt cttggccgca gcctataaca actttcggaa     420
gagcatggac agcataggaa agaagcaata tcaggtccag catgggtcct gcagctacac     480
tttcctcctg ccagagatgg acaactgccg ctcttcctcc agccctacg tgtccaatgc      540 tgtgcagagg gacgcgccgc tcgaatacga tgactcggtg cagaggctgc aagtgctgga    600
gaacatcatg gaaacaaca ctcagtggct aatgaagctt gagaattata tccaggacaa     660
catgaagaaa gaaatggtag agatacagca gaatgcagta cagaaccaga cggctgtgat   720
gatagaaata gggacaaacc tgttgaacca acagctgag caaacgcgga agttaactga    780
tgtggaagcc caagtattaa atcagaccac gagacttgaa cttcagctct ggaacactc    840 cctctcgaca aacaaattgg aaaaacagat tttggaccag accagtgaaa taaacaaatt    900
gcaagataag aacagtttcc tagaaaagaa ggtgctagct atggaagaca agcacatcat   960
ccaactacag tcaataaaag aagagaaaga tcagctacag gtgttagtat ccaagcaaaa   1020
ttccatcatt gaagaactag aaaaaaaaat agtgactgcc acggtgaata attcagttct   1080
tcaaaagcag caacatgatc tcatgggac agttaataac ttactgacta tgatgtccac    1140
atcaaactca gctaaggacc ccactgttgc taaagaagaa caaatcagct tcagagactg   1200
tgctgaagta ttcaaatcag gacacaccac aaatggcatc tacacgttaa cattccctaa   1260
ttctacagaa gagatcaagg cctactgtga catggaagct ggaggaggcg ggtggacaat   1320
tattcagcga cgtgaggatg gcagcgttga ttttcagagg acttggaaag aatataaagt   1380
gggatttggt aacccttcag gagaatattg gctgggaaat gagtttgttt cgcaactgac   1440
taatcagcaa cgctatgtgc ttaaaataca ccttaaagac tgggaaggga atgaggctta   1500
ctcattgtat gaacatttct atctctcaag tgaagaactc aattatagga ttcaccttaa   1560
aggacttaca gggacagccg gcaaaataag cagcatcagc caaccaggaa atgattttag   1620
cacaaaggat ggagacaacg acaaatgtat ttgcaaatgt tcacaaatgc taacaggagg   1680
ctggtggttt gatgcatgtg gtccttccaa cttgaacgga atgtactatc cacagaggca   1740
gaacacaaat aagttcaacg gcattaaatg gtactactgg aaaggctcag gctattcgct   1800
caaggccaca accatgatga tccgaccagc agatttctaa acatcccagt ccacctgagg   1860
aactgtctcg aactatttc aaagacttaa gcccagtgca ctgaaagtca cggctgcgca   1920
ctgtgtcctc ttccaccaca gagggcgtgt gctcggtgct gacgggaccc acatgctcca   1980
gattagagcc tgtaaacttt atcacttaaa cttgcatcac ttaacggacc aaagcaagac   2040
cctaaacatc cataattgtg attagacaga acacctatgc aaagatgaac ccgaggctga   2100
gaatcagact gacagtttac agacgctgct gtcacaacca agaatgttat gtgcaagttt   2160
atcagtaaat aactggaaaa cagaacactt atgttataca atacagatca tcttggaact   2220
gcattcttct gagcactgtt tatacactgt gtaaataccc atatgtcct              2269
```

<210> SEQ ID NO 10
<211> LENGTH: 496
<212> TYPE: PRT
<213> ORGANISM: Homo sapiens

<400> SEQUENCE: 10

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30
```

-continued

```
Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Thr Gln Trp Leu Met Lys
            85                  90                  95

Leu Glu Asn Tyr Ile Gln Asp Asn Met Lys Lys Glu Met Val Glu Ile
            100                 105                 110

Gln Gln Asn Ala Val Gln Asn Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
```

|  | 450 | 455 | 460 |  |
|---|---|---|---|---|
| Asn Thr Asn Lys Phe Asn Gly Ile Lys Trp Tyr Tyr Trp Lys Gly Ser |
| 465 | | 470 | | 475 | | 480 |
| Gly Tyr Ser Leu Lys Ala Thr Thr Met Met Ile Arg Pro Ala Asp Phe |
| | | 485 | | | 490 | | | 495 |

<210> SEQ ID NO 11
<211> LENGTH: 2424
<212> TYPE: DNA
<213> ORGANISM: Mus musculus
<220> FEATURE:
<221> NAME/KEY: misc_feature
<222> LOCATION: (2308)..(2308)
<223> OTHER INFORMATION: n is a, c, g, or t

<400> SEQUENCE: 11

| ggctgctcct | tcctctcagg | acagctccga | gtgtgccggg | gagaagagaa | gagaagagac | 60 |
|---|---|---|---|---|---|---|
| aggcactggg | aaagagcctg | ctgcgggacg | gagaaggctc | tcactgatgg | acttattcac | 120 |
| acggcacagc | cctgtgcctt | agacagcagc | tgagagctca | ggacgcaagt | ttgctgaact | 180 |
| cacagtttag | aacccaaaaa | gagagagaga | atgtggcaga | tcattttcct | aacttttggc | 240 |
| tgggatcttg | tcttggcctc | agcctacagt | aactttagga | gagcgtggaa | cagcacaggc | 300 |
| agaaggcagt | accaggtcca | gaacggaccc | tgcagctaca | cgttcctgct | gccggagacc | 360 |
| gacagctgcc | gatcttcctc | cagcccctac | atgtccaatg | ccgtgcagag | ggatgcaccc | 420 |
| ctcgactacg | acgactcagt | gcaaaggctg | caggtgctgg | agaacattct | agagaacaac | 480 |
| acacagtggc | tgatgaagct | ggagaattac | attcaggaca | catgaagaa | ggagatggtg | 540 |
| gagatccaac | agaatgtggt | gcagaaccag | acagctgtga | tgatagagat | tggaaccagc | 600 |
| ttgctgaacc | agacagcagc | acaaactcgg | aaactgactg | atgtggaagc | ccaagtacta | 660 |
| aaccagacga | caagactcga | gctgcagctt | ctccaacatt | ctatttctac | caacaaattg | 720 |
| gaaaagcaga | ttttggatca | gaccagtgaa | ataaacaagc | tacaaaataa | gaacagcttc | 780 |
| ctagaacaga | aagttctgga | catggagggc | aagcacagcg | agcagctaca | gtccatgaag | 840 |
| gagcagaagg | acgagctcca | ggtgctggtg | tccaagcaga | gctctgtcat | tgacgagctg | 900 |
| gagaagaagc | tggtgacagc | cacggtcaac | aactcgctcc | ttcagaagca | gcagcatgac | 960 |
| ctaatggaga | ccgtcaacag | cttgctgacc | atgatgtcat | cacccaactc | caagagctcg | 1020 |
| gttgctatcc | gtaaagaaga | gcaaaccacc | ttcagagact | gtgcggaaat | cttcaagtca | 1080 |
| ggactcacca | ccagtggcat | ctacacactg | accttcccca | actccacaga | ggagatcaag | 1140 |
| gcctactgtg | acatggacgt | gggtggagga | gggtggacag | tcatccaaca | ccgagaagat | 1200 |
| ggcagtgtga | cttccagag | gacgtggaaa | gaatacaaag | agggcttcgg | gaaccctctg | 1260 |
| ggagagtact | ggctgggcaa | tgagtttgtc | tcccagctga | ccggtcagca | ccgctacgtg | 1320 |
| cttaagatcc | agctgaagga | ctgggaaggc | aacgaggcgc | attcgctgta | tgatcacttc | 1380 |
| tacctcgctg | gtgaagagtc | caactacagg | attcacctta | caggactcac | ggggaccgcg | 1440 |
| gccaaaataa | gtagcatcag | ccaaccagga | agtgatttta | gcacaaagga | ttcggacaat | 1500 |
| gacaaatgca | tctgcaagtg | ttcccagatg | ctctcaggag | ctggtggtt | tgacgcatgt | 1560 |
| ggtccttcca | acttgaatgg | acagtactac | ccacaaaaac | agaatacaaa | taagtttaac | 1620 |
| ggtatcaagt | ggtactactg | gaaggggtcc | ggctactcgc | tcaaggccac | aaccatgatg | 1680 |
| atccggccag | cagatttcta | aatgcctgcc | tacactacca | gaagaacttg | ctgcatccaa | 1740 |
| agattaactc | caaggcactg | agagacacca | gtgcatagca | gccccttcc | acatcaggaa | 1800 |

-continued

```
gtgctcctgg gggtggggag ggtctgtgtg taccagactg aagcgcatca cttaagcctg    1860
caccgctaac caaccaaagg cactgcagtc tggagaaaca cttctgggaa ggttgtggct    1920
gaggatcaga aggacagcgt gcagactctg tcacaaggaa gaatgttccg tgggagttca    1980
gcagtaaata actggaaaac agaacactta gatggtgcag ataaatcttg ggaccacatt    2040
cctctaagca cggtttctag agtgaataca ttcacagctc ggctgtcaca atgcaaggc     2100 cgtgtcctcg cactgtggca gccagtatcc agggacttct aagtggtggg cacaggctat    2160
catctggaga agcacacatt cattgttttc ctcttgggtg cttaacatgt tcatttgaaa    2220
acaacacatt tacctatctt gatggcttag tttttaatgg ctggctacta tttactatat    2280
ggcaaaaatg cccacatctc tggaatancc accaaataag cgccatgttg gtgaatgcgg    2340
aggctgtact attttgtttt cttcctggct ggtaaatatg aaggtatttt tagtaattaa    2400
atataagtta ttagttgaaa gacc                                           2424
```

<210> SEQ ID NO 12
<211> LENGTH: 496
<212> TYPE: PRT
<213> ORGANISM: Mus musculus

<400> SEQUENCE: 12

```
Met Trp Gln Ile Ile Phe Leu Thr Phe Gly Trp Asp Leu Val Leu Ala
1               5                   10                  15

Ser Ala Tyr Ser Asn Phe Arg Lys Ser Val Asp Ser Thr Gly Arg Arg
            20                  25                  30

Gln Tyr Gln Val Gln Asn Gly Pro Cys Ser Tyr Thr Phe Leu Leu Pro
        35                  40                  45

Glu Thr Asp Ser Cys Arg Ser Ser Ser Pro Tyr Met Ser Asn Ala
    50                  55                  60

Val Gln Arg Asp Ala Pro Leu Asp Tyr Asp Ser Val Gln Arg Leu
65                  70                  75                  80

Gln Val Leu Glu Asn Ile Leu Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Val Val Gln Asn Gln Thr Ala Val Met Ile Glu Ile Gly
        115                 120                 125

Thr Ser Leu Leu Asn Gln Thr Ala Ala Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Gln His Ser Ile Ser Thr Asn Lys Leu Glu Lys Gln Ile Leu Asp
                165                 170                 175

Gln Thr Ser Glu Ile Asn Lys Leu Gln Asn Lys Asn Ser Phe Leu Glu
            180                 185                 190

Gln Lys Val Leu Asp Met Glu Gly Lys His Ser Glu Gln Leu Gln Ser
        195                 200                 205

Met Lys Glu Gln Lys Asp Glu Leu Gln Val Leu Val Ser Lys Gln Ser
    210                 215                 220

Ser Val Ile Asp Glu Leu Glu Lys Lys Leu Val Thr Ala Thr Val Asn
225                 230                 235                 240

Asn Ser Leu Leu Gln Lys Gln Gln His Asp Leu Met Glu Thr Val Asn
                245                 250                 255
```

```
Ser Leu Leu Thr Met Met Ser Ser Pro Asn Ser Lys Ser Ser Val Ala
            260                 265                 270

Ile Arg Lys Glu Glu Gln Thr Thr Phe Arg Asp Cys Ala Glu Ile Phe
            275                 280                 285

Lys Ser Gly Leu Thr Thr Ser Gly Ile Tyr Thr Leu Thr Phe Pro Asn
            290                 295                 300

Ser Thr Glu Glu Ile Lys Ala Tyr Cys Asp Met Asp Val Gly Gly Gly
305                 310                 315                 320

Gly Trp Thr Val Ile Gln His Arg Glu Asp Gly Ser Val Asp Phe Gln
                325                 330                 335

Arg Thr Trp Lys Glu Tyr Lys Glu Gly Phe Gly Asn Pro Leu Gly Glu
            340                 345                 350

Tyr Trp Leu Gly Asn Glu Phe Val Ser Gln Leu Thr Gly Gln His Arg
            355                 360                 365

Tyr Val Leu Lys Ile Gln Leu Lys Asp Trp Glu Gly Asn Glu Ala His
            370                 375                 380

Ser Leu Tyr Asp His Phe Tyr Leu Ala Gly Glu Glu Ser Asn Tyr Arg
385                 390                 395                 400

Ile His Leu Thr Gly Leu Thr Gly Thr Ala Ala Lys Ile Ser Ser Ile
            405                 410                 415

Ser Gln Pro Gly Ser Asp Phe Ser Thr Lys Asp Ser Asp Asn Asp Lys
            420                 425                 430

Cys Ile Cys Lys Cys Ser Gln Met Leu Ser Gly Gly Trp Trp Phe Asp
            435                 440                 445

Ala Cys Gly Pro Ser Asn Leu Asn Gly Gln Tyr Tyr Pro Gln Lys Gln
            450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
            485                 490                 495

<210> SEQ ID NO 13
<211> LENGTH: 24
<212> TYPE: DNA
<213> ORGANISM: Primer Sequence

<400> SEQUENCE: 13
acaatgacag ttttcctttc cttt                                          24

<210> SEQ ID NO 14
<211> LENGTH: 24
<212> TYPE: DNA
<213> ORGANISM: Primer Sequence

<400> SEQUENCE: 14
tgtgtccatg agctccagtt gttg                                          24

<210> SEQ ID NO 15
<211> LENGTH: 24
<212> TYPE: DNA
<213> ORGANISM: Primer Sequence

<400> SEQUENCE: 15
aaatggtttc tcttcttctc tttt                                          24

<210> SEQ ID NO 16
<211> LENGTH: 24
<212> TYPE: DNA
```

-continued

```
<213> ORGANISM: Primer Sequence

<400> SEQUENCE: 16
cgagactgtg cagatgtata tcaa                                              24

<210> SEQ ID NO 17
<211> LENGTH: 24
<212> TYPE: DNA
<213> ORGANISM: Primer Sequence

<400> SEQUENCE: 17
tcttctccct ccgttttctg gatt                                              24

<210> SEQ ID NO 18
<211> LENGTH: 24
<212> TYPE: DNA
<213> ORGANISM: Primer Sequence

<400> SEQUENCE: 18
agtatggact ctttagccgg ctta                                              24

<210> SEQ ID NO 19
<211> LENGTH: 24
<212> TYPE: DNA
<213> ORGANISM: Primer Sequence

<400> SEQUENCE: 19
catctttccc cctccgaggt ctgc                                              24
```

US 7,427,594 B1

METHODS AND PHARMACEUTICALS COMPOSITIONS FOR TREATING CORONARY ARTERY DISEASE, ISCHEMIA, AND VASCULAR DISEASE USING ANGIOPOIETINS

CROSS REFERENCE TO RELATED APPLICATIONS

This application claims priority to U.S. Provisional Ser. No. 60/359,679 filed Feb. 26, 2002, which is incorporated herein by reference.

FIELD OF THE INVENTION

The present invention relates activities of Angiopoietin-1 (Ang-1) and Angiopoietin-2 (Ang-2) and to uses of compounds having such activities to treat diseases and disorders and find additional compounds.

BACKGROUND OF THE INVENTION

Angiogenesis plays an important role in embryogenesis and tumorigenesis. It is a complicated multistep process, which includes the dynamic changes of cell-cell and cell-matrix interactions, endothelial cell proliferation and migration, recruitment of the peri-vascular supporting cells, and the maturation process. Numerous molecules are involved in those processes, including growth factors and their receptors, proteases, adhesion receptors, and the ECM1 components. VEGF and angiopoietin families play special roles in angiogenesis due to the restricted expression of their receptors.

Ang-1 and Ang-2 are ~70 kDa with a considerable sequence homology, which consists of a signal peptide, an N-terminal coiled-coil domain, a short linker peptide region, and a C-terminal fibrinogen homology domain (FHD). The coiled-coil region is responsible for dimerization/multimerization of angiopoietins, and the fibrinogen homology domain binds to Tie-2 receptor. Both Ang-1 and Ang-2 form dimers and oligomers.

Ang-1 and Ang-2 are the unique antagonists. Ang-1 induces tyrosine phosphorylation of Tie-2 receptor and promotes recruitment of the pericytes and smooth muscle cells, thereby playing a role in establishing and maintaining the vascular integrity and quiescence. As an antagonist of Ang-1, Ang-2 competes with Ang-1 for binding of Tie-2, blocks the phosphorylation of Tie-2 receptors induced by Ang-1, and loosens the interactions between endothelial and peri-vascular support cells and ECM.

Targeted disruption of Ang-1 and Tie-2 and overexpression of Ang-2 resulted in embryonic death with the similar vascular defects. Those mice have normal primary vascular development, but the remodeling and maturation of the vasculature are defective. The transgenic mice overexpressing Ang-1 displayed increased vascularization and decreased adult vasculature leakage. Together, those results indicated that Ang-1 plays an indispensable role in the formation of blood vessels during mouse development by recruiting and maintaining peri-endothelial support cells.

Several studies have offered possible mechanisms for the pro-angiogenic effect of Ang-1. Although Ang-1 does not stimulate the proliferation of endothelial cells, it stimulates endothelial cell migration, induces the capillary-like tubule formation, and promotes survival of endothelial cells. Ang-1 inhibits apoptosis of the endothelial cells via phosphatidylinositol 3-kinase/Akt pathway.

Angiogenesis is regulated by the precise balance between pro- and anti-angiogenic factors. Ang-2 expression is often induced in the endothelia undergoing active remodeling or regression and by hypoxia and several growth factors, including VEGF. Ang-2 destabilizes the vasculature. Thus, it initiates angiogenesis in the presence of VEGF, which supplies endothelial cells with necessary survival and proliferation signals, or induces apoptosis of endothelial cells in the absence of the pro-angiogenic factors.

SUMMARY OF THE INVENTION

One aspect of the present invention relates to pharmaceutical compositions that comprise a pharmaceutically acceptable carrier and either a therapeutically effective amount of an ECM-binding fragment of Ang-1 protein that comprises SEQ ID NO:1 and/or SEQ ID NO:2 or a homologous peptide thereof.

Another aspect of the present invention relates to pharmaceutical compositions that comprise a pharmaceutically acceptable carrier and a vector comprising a nucleic acid molecule that comprises the nucleotide sequence that encodes an ECM-binding fragment of Ang-1 protein that comprises SEQ ID NO:1 and/or SEQ ID NO:2 or a homologous peptide thereof.

A further aspect of the present invention provide methods of treating an individual suspected of having coronary artery disease, vascular disease or a condition involving ischemia. In some embodiments, the methods comprise the step of administering to the individual a pharmaceutical composition that comprises a therapeutically effective amount of an ECM-binding fragment of Ang-1 protein that comprises SEQ ID NO:1 and/or SEQ ID NO:2 or a homologous peptide thereof. In some embodiments, the methods comprise the step of administering to the individual pharmaceutical compositions that comprises a vector comprising a nucleic acid molecule that comprises the nucleotide sequence that encodes an ECM-binding fragment of Ang-1 protein that comprises SEQ ID NO:1 and/or SEQ ID NO:2 or a homologous peptide thereof.

Another aspect of the invention provides methods of promoting angiogenesis, endothelial survival and maintaining vascular integrity in an individual. In some embodiments, the methods comprise the step of administering to the individual a pharmaceutical composition that comprises a therapeutically effective amount of an ECM-binding fragment of Ang-1 protein that comprises SEQ ID NO:1 and/or SEQ ID NO:2 or a homologous peptide thereof. In some embodiments, the methods comprise the step of administering to the individual pharmaceutical compositions that comprises a vector comprising a nucleic acid molecule that comprises the nucleotide sequence that encodes an ECM-binding fragment of Ang-1 protein that comprises SEQ ID NO:1 and/or SEQ ID NO:2 or a homologous peptide thereof.

According to some other aspects of the invention, methods are provided to identify compounds that modulates binding of Ang-1 to ECM. The methods comprise performing a test assay that comprises the steps of contacting a protein that comprises at least an ECM-binding fragment of Ang-1 protein that comprises SEQ ID NO:1 and/or SEQ ID NO:2 with ECM material in the presence of a test compound, then measuring the level of binding of the protein that comprises at least an ECM-binding fragment of Ang-1 protein that comprises SEQ ID NO:1 and/or SEQ ID NO:2 with the ECM; and then comparing the level with the level of binding of protein that comprises at least an ECM-binding fragment of Ang-1 protein that comprises SEQ ID NO:1 and/or SEQ ID NO:2 with ECM material in the absence of the test compound.

When the level of binding of the protein that comprises at least an ECM-binding fragment of Ang-1 protein that comprises SEQ ID NO:1 and/or SEQ ID NO:2 with the ECM in the presence of the test compound is less than the level of binding of the protein that comprises at least an ECM-binding fragment of Ang-1 protein that comprises SEQ ID NO:1 and/or SEQ ID NO:2 with the ECM in the absence of the test compound results indicate that the test compound modulates binding of Ang-1 to ECM by inhibiting the binding. When the level of binding of the protein that comprises at least an ECM-binding fragment of Ang-1 protein that comprises SEQ ID NO:1 and/or SEQ ID NO:2 with the ECM in the presence of the test compound is more than the level of binding of the protein that comprises at least an ECM-binding fragment of Ang-1 protein that comprises SEQ ID NO:1 and/or SEQ ID NO:2 with the ECM in the absence of the test compound results indicate that the test compound modulates binding of Ang-1 to ECM by enhancing the binding.

A further aspect of the invention provides pharmaceutical compositions which comprise a therapeutically effective amount of Ang-2 protein and/or a vector comprising a nucleic acid molecule that comprises the nucleotide coding sequence of Ang-2.

Additional aspects of the invention provide for methods of treating an individual suspected of having cancer. The methods comprise the step of administering to the individual a pharmaceutical composition comprising a pharmaceutical composition which comprise a therapeutically effective amount of Ang-2 protein and/or a vector comprising a nucleic acid molecule that comprises the nucleotide coding sequence of Ang-2.

BRIEF DESCRIPTION OF THE FIGURES

In FIG. 3A, the purified v5-tagged Ang-1 proteins (500 ng/ml) were loaded onto a heparin-Sepharose CL-6B affinity column. The flow-through was collected, and the column was washed with 0.15, 0.3, 0.5, and 1 M sodium chloride (NaCl, FIG. 3A, lanes 3-6), and the eluted proteins were collected. All the collected fractions were subjected to Western blot analysis using anti-v5 antibody. The results indicated that Ang-1v5 does not bind to heparin-Sepharose, and all the v5-tagged Ang-1 was in the flow-through fraction (FIG. 3A, lane 2). Lane 1 in FIG. 3A represents the starting materials. In FIG. 3B, the ECM proteins were extracted, and Western blot analysis was performed after the incubation of the confluent LLC cells expressing Ang-1 with serum-free cell culture media containing heparin (200 µg/ml, FIG. 3B, lane 2), chondroitin sulfate (200 µg/ml, FIG. 3B, lane 3), or SFM alone (FIG. 3B, lane 1) for 12 h. Molecular mass markers are as indicated.

DETAILED DESCRIPTION OF PREFERRED EMBODIMENTS

Figure 1:
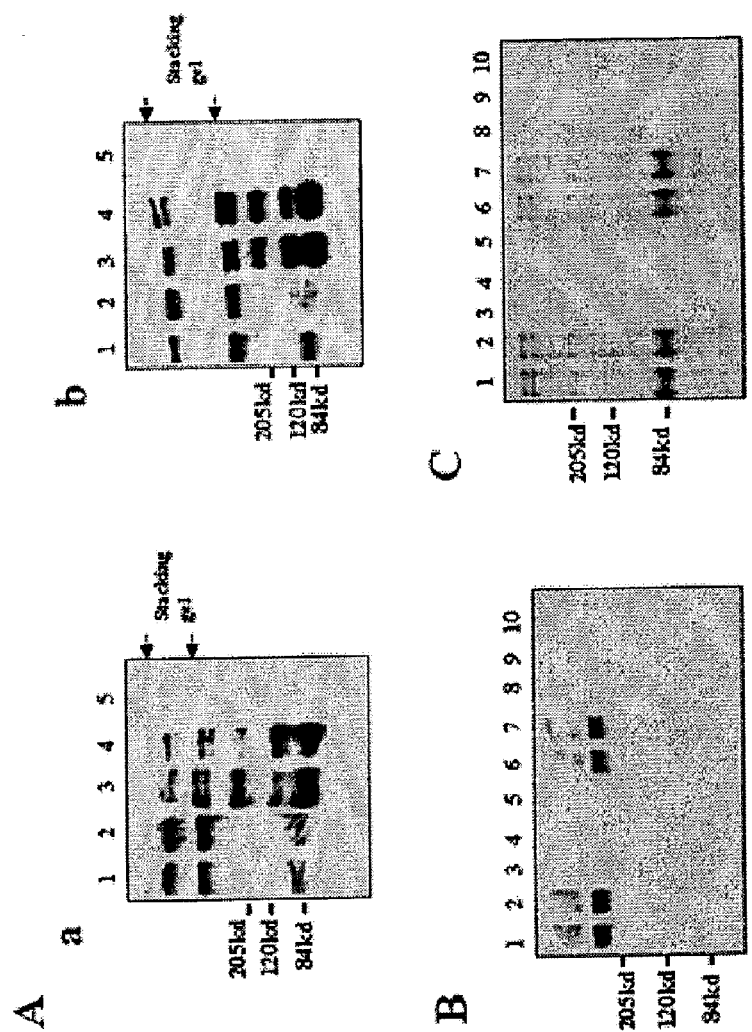
FIGS. 1Aa, 1Ab, 1B and 1C disclose data related to angiopoietin-1 incorporated into the extracellular matrix. The expression of Ang-1 and Ang-2 in the serum-free conditioned media (FIGS. 1Aa, 1Ab) and in the ECM (FIG. 1B) by the transfected LLC and TA3 cells were determined by Western blot analyses using anti-v5 antibody (Invitrogen). The Western blot analyses were performed under non-reducing conditions using the concentrated serum-free media (FIGS. 1Aa, 1Ab) or the ECM extracts (FIG. 1B) derived from two independent isolates of the transfected LLC cells expressing Ang-1v5 (FIG. 1Aa lanes 1 and 2, and FIG. 1B, lanes 1 and 2) or Ang-2v5 (FIG. 1Aa lanes 3 and 4, FIG. 1B lanes 3 and 4); two independent isolates of the transfected TA3 cells expressing Ang-1v5 (FIG. 1Ab lanes 1 and 2, FIG. 1B lanes 6 and 7) or Ang-2v5 (FIG. 1Ab lanes 3 and 4, FIG. 1B lanes 8 and 9), and the tumor cells transfected with the expression vector only (LLC, carcinoma cells, FIG. 1Aa lane 5, FIG. 1B, lane 5; and TA3 cells, FIG. 1Ab lane 5, FIG. 1B, lane 10).
FIG. 1C, the same protein samples in the FIG. 1B were subjected to—mercaptoethanol (5%) treatment. Molecular mass markers are as indicated. kd indicates kilodalton.

As used herein, the term "ECM" refers to the extracellular matrix. The extracellular matrix (ECM) is a complex structural entity surrounding and supporting cells that are found within mammalian tissues. The ECM is comprises, structural proteins (collagen and elastin), specialized proteins (e.g. fibrillin, fibronectin, and laminin), and proteoglycans. Proteoglycans are composed of a protein core to which is attached long chains of repeating disaccharide units termed of glycosaminoglycans (GAGs) forming extremely complex high molecular weight components of the ECM.

The present invention relates to peptides and methods using those peptides to treat an individual suspected of having cancer, coronary artery disease, ischemias, and other vascular diseases. Although the specific procedures and methods described herein are exemplified using several specific peptides derived from Angiopoietin-1 and -2, they are merely illustrative for the practice of the invention. Analogous procedures and techniques, as well as functionally equivalent peptides and peptide homologues, as will be apparent to those of skill in the art based on the detailed disclosure provided herein are also encompassed by the invention.

Aspects of the present invention arises from the discovery that angiopoietin-1 (Ang-1) associates with extracellular matrix (ECM), and the function of Ang-1 is regulated by the association with the ECM. Thus, while Ang-1 promotes angiogenesis when not associated with the ECM, it is inhibited from promoting angiogenesis while associated with the ECM.

According to some embodiments the present invention provides for pharmaceutical compositions comprising a pharmaceutically acceptable carrier and a therapeutically effective amount of an ECM-binding fragment of the Ang-1 protein and/or a vector comprising a nucleic acid molecule that comprises the nucleotide sequence that encodes an ECM-binding fragment of Ang-1 protein.

As used herein, the term "ECM-binding fragment of Ang-1 protein" refers to any peptide sequence that comprises a peptide fragment from Ang-1 that can bind to the ECM. In some embodiments the ECM-binding fragment of Ang-1 protein is the 26-mer peptide VHNLVSLCTKEGVLLKG-GKREEEKPF (SEQ ID NO:1). In some embodiments the ECM binding fragment of Ang-1 protein is VHNLVNLCT-KEGVLLKGGKREEEKPF (SEQ ID NO:2). The fragment may be the entire Ang-1 protein or it may be a fragment of the Ang-1 protein. In some embodiments, the ECM-binding fragment of Ang-1 protein may be a part of a fusion protein that comprises Ang-1 protein sequence and non-Ang-1 protein sequence. In some embodiments the ECM-binding fragment of Ang-1 protein is at least 26, at least 50, at least 75, at least 100, at least 500, at least 1000 amino acid residues long. In some embodiments the ECM-binding fragment of Ang-1 protein comprises SEQ ID NO:4, SEQ ID NO:6, and/or SEQ ID NO:8

As used herein, the term "homologous peptide" refers to a peptide that has at least 50% similarity to the peptide being referred to. In some embodiments the peptide has at least 60%, at least 70%, at least 80%, at least 90%, at least 95%, at least 96%, at least 97%, at least 98%, at least 99%, or at least 100% similarity to the ECM-binding fragment of Ang-1 protein and can bind to the ECM. In some embodiments the homologous peptide has at least 60%, at least 70%, at least 80%, at least 90%, at least 95%, at least 96%, at least 97%, at least 98%, at least 99%, or at least 100% similarity to SEQ ID NO:1, SEQ ID NOs:2, SEQ ID NO:4, SEQ ID NO:6, and/or SEQ ID NO:8. The homologous peptide may be isolated or incorporated into another protein so that a fusion protein is created.

According to some embodiments a homologous peptide refers to a peptide that has conservative substitutions. A conservative substitution is recognized in the art as a substitution of one amino acid for another amino acid that has similar properties. I some embodiments examples of conservative substitutions are those that are described in Table I.

TABLE I

| Amino Acid | Conservative Changes |
|---|---|
| Alanine (A) | Glycine (G), Serine (S) |
| Aspartic Acid (D) | Glutamic Acid (B) |
| Glutamic Acid (E) | Aspartic Acid (D) |
| Phenylalanine (F) | Tryptophan (W), Tyrosine (Y) |
| Glycine (G) | Alanine (A) |
| Histidine (H) | Tyrosine (Y) |
| Isoleucine (I) | Leucine (L), Methionine (M), Valine (V) |
| Lysine (K) | Arginine (R) |
| Leucine (L) | Isoleucine (1), Methionine (M) Valine (V) |
| Methionine (M) | Isoleucine (1), Leucine (L), Valine (V) |
| Asparagine (N) | Glutamine (Q) |
| Glutamine (Q) | Asparagine (N) |

TABLE I-continued

| Amino Acid | Conservative Changes |
| --- | --- |
| Arginine (R) | Lysine (K) |
| Serine (S) | Alanine (A), Threonine (T) |
| Threonine (T) | Serine (S) |
| Valine (V) | Isoleucine (I), Methionine (M) Valine (V) |
| Tryptophan (W) | Phenylalanine (F), Tyrosine (Y) |
| Tyrosine (Y) | Phenylalanine (F) Histidine (H) Tryptophan (W) |

As used herein, the phrase "homologous", "homologous peptide", "homologous peptide thereof" or variations thereof, refers to sequences characterized by a homology, at the nucleotide level or amino acid level, of at least a specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. Homologous amino acid sequences include those amino acid sequences which contain conservative amino acid substitutions and which polypeptides have the same binding and/or activity.

Percent homology, similarity, or identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology between the probe and target is between about 50% to about 60%. In some embodiments, nucleic acids have nucleotides that are about 60%, preferably about 70%, more preferably about 80%, more preferably about 85%, more preferably about 90%, more preferably about 92%, more preferably about 94%, more preferably about 95%, more preferably about 97%, more preferably about 98%, more preferably about 99% and most preferably about 100% homologous to nucleotide sequences disclosed herein.

Homology may also be at the polypeptide level. In some embodiments, polypeptides are about 50%, about 60%, preferably about 70%, more preferably about 80%, more preferably about 85%, more preferably about 90%, more preferably about 92%, more preferably about 94%, more preferably about 95%, more preferably about 97%, more preferably about 98%, more preferably about 99% and most preferably about 100% homologous to the polypeptide sequences disclosed herein.

As used herein, the term "fusion protein" refers to a protein that comprises amino acids that are from at least two different proteins. As an example, a fusion protein may comprise the ECM-binding fragment of Ang-1 protein and kinase domain of another protein. This example would be considered a fusion protein. The fusion of two protein sequences can be in any orientation. The ECM-binding fragment may be placed at the N-terminus of a fusion protein or at the C-terminus of a fusion protein. In some embodiments, the ECM-binding fragment of Ang-1 protein may be placed in the middle of a protein.

As used herein, the term "homologous peptide thereof" refers to a peptide that is a homologous peptide, as defined above, to the ECM-binding fragment of Ang-1 protein. The homologous peptide thereof may be fusion protein, the entire Ang-1 protein, or a fragment thereof.

As used herein, the term "nucleotide sequence that encodes an ECM-binding fragment of Ang-1 protein" refers to a nucleotide sequence that when transcribed and translated would comprise an ECM-binding fragment of Ang-1 protein. According to some embodiments of the present invention, the nucleotide sequence may be the entire sequence of Ang-1. In some embodiments the nucleotide sequence may comprise a fragment of the nucleotide sequence of Ang-1. In some embodiments the nucleotide sequence that encodes an ECM-binding fragment of Ang-1 protein comprises SEQ ID NOs: 3, 5, and/or 7. The nucleotide sequence of Ang-1 is well known to one of ordinary skill in the art.

As used herein, the term "pharmaceutical composition" refers to compositions according to the invention including delivery components in combination with nucleic acid molecules and/or peptide molecules which further comprise a pharmaceutically acceptable carriers or vehicles, such as, for example, saline. Any medium may be used which allows for successful delivery of the peptide and/or nucleic acid. One skilled in the art would readily comprehend the multitude of pharmaceutically acceptable media that may be used in the present invention.

Pharmaceutical compositions may be formulated by one having ordinary skill in the art with compositions selected depending upon the chosen mode of administration. Suitable pharmaceutical carriers are described in Remington's Pharmaceutical Sciences, A. Osol, a standard reference text in this field, which is incorporated herein by reference.

The pharmaceutical compositions of the present invention may be administered by any means that enables the active agent to reach the agent's site of action in the body of an individual. Pharmaceutical compositions may be administered parenterally, i.e., intratumor, intravenous, subcutaneous, intramuscular. Intravenous and intratumor administration are preferred routes. Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

As used herein, the term "vector" refers to a delivery vehicle that is capable of delivering a nucleic acid to a cell. In some embodiments, the vector is a viral vector. In general, viral vectors may be DNA viruses such as recombinant adenoviruses and recombinant vaccinia viruses or RNA viruses such as recombinant retroviruses. Other recombinant vectors include recombinant prokaryotes that can infect cells and express recombinant genes. In addition to recombinant vectors, other vectors are also contemplated such as encapsulation in liposomes, lipofectin-mediated transfection, transferrin-mediated transfection and other receptor-mediated means. In some embodiments the vector is a DNA plasmid. The invention is intended to include such other forms of expression vectors and other suitable delivery means which serve equivalent functions and which become known in the art subsequently hereto.

Examples of recombinant adenoviral vectors include those which have the E1a region deleted and which carry a temperature-sensitive mutation in E2a (Engelhardt et al., Hum Gene Ther 5:1217-1229, 1994, which is incorporated herein by reference). Other examples of recombinant adenoviral vectors useful to deliver nucleic acid sequence of the present invention are described in U.S. Pat. Nos. 5,756,283 and 5,707,618, which are each incorporated herein by reference.

In another preferred embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In another preferred embodiment of the present invention, nucleic acid is delivered through folate receptor means. The nucleic acid sequence to be delivered to a host cell is linked to polylysine and the complex is delivered to the tumor cell by means of the folate receptor. U.S. Pat. No. 5,108,921 issued Apr. 28, 1992 to Low et al., which is incorporated herein by reference, describes such delivery components.

In another preferred embodiment of the present invention, nucleic acid is delivered through the use of lipofectin-mediated DNA transfer. LipofectAMINE™ liposome reagent (Life Technologies, Gaithersburg Md.) is a commercially available liposome encapsulation reagent which can be used for encapsulating cells following manufacturer's instructions. LipofectAMINE™ liposome reagent encapsulated nucleic acid molecules may be delivered to a host cell using liposome formulation administration methods.

In another preferred embodiment of the present invention, nucleic acid is delivered through the use of cationic lipid-mediated DNA transfer such as that which is described in U.S. Pat. No. 5,703,055, which is incorporated herein by reference.

In another preferred embodiment of the present invention, nucleic acid is delivered through the use of liposome-mediated DNA transfer such as that which is described in U.S. Pat. Nos. 4,235,871, 4,241,046 and 4,394,448, which are each incorporated herein by reference.

According to some embodiments the present invention provides methods of treating an individual suspected of having coronary artery disease, vascular disease, or a condition involving ischemia. In some embodiments the method comprises the steps of administering to the individual a pharmaceutical composition comprising a pharmaceutically acceptable carrier and a therapeutically effective amount of an ECM-binding fragment of Ang-1 protein that comprises SEQ ID NO: 1 and/or SEQ ID NO:2 or a homologous peptide thereof and/or a vector comprising a nucleic acid molecule that comprises the nucleotide sequence that encodes an ECM-binding fragment of Ang-1 protein that comprises SEQ ID NO:1 and/or SEQ ID NO:2 or a homologous peptide thereof. In some embodiments, the methods are provided for individuals need thereof.

As used herein, the term "coronary artery disease" refers to diseases that are a result of the buildup of cholesterol in the inside layers of the arteries. As used herein, the term "vascular disease" refers to diseases that is related to the circulatory system. As used herein, the term "ischemia" refers to a condition that is a caused by a lack of blood flow that would otherwise be present in a healthy individual.

In some embodiments the compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g, containing conventional suppository bases such as cocoa butter or other glycerides.

In addition to the formulations described previously, the compounds may also be formulated as a depot preparation.

Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and/or nucleotides of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

According to some embodiments of the present invention the pharmaceutical composition is administered in an amount that is therapeutically effective. As used herein, the term "therapeutically effective" refers to an amount effective to achieve the intended purpose. In some embodiments the intended purpose is to treat coronary artery disease, vascular disease, a condition involving ischemia, or cancer. In some embodiments a therapeutically effective amount refers to an amount effective to ameliorate or prevent the symptoms, or prolong the survival of, the patient being treated. Therapeutically effective amounts are typically determined by the effect they have compared to the effect observed when a composition which includes no active ingredient is administered to a similarly situated individual The precise effective amount for a subject will depend upon the subject's size and health, the nature and extent of the condition, and the therapeutics or combination of therapeutics selected for administration. However, the effective amount for a given situation is determined by routine experimentation and is within the judgment of the clinician. Determination of a therapeutically effective amount is well within the capabilities of those skilled in the art, especially in light of the detailed disclosure provided herein.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

According to some embodiments, the present invention provides for methods of promoting angiogenesis, endothelial survival, and/or maintaining vascular integrity comprising the administration of a pharmaceutical composition comprising a pharmaceutically acceptable carrier and a therapeutically effective amount of an ECM-binding fragment of Ang-1 protein that comprises SEQ ID NO:1 and/or SEQ ID NO:2 or a homologous peptide thereof and/or a vector comprising a nucleic acid molecule that comprises the nucleotide sequence that encodes an ECM-binding fragment of Ang-1 protein that comprises SEQ ID NO:1 and/or SEQ ID NO:2 or a homologous peptide thereof.

As used herein, the term "angiogenesis" refers to the growth of blood vessels. In some embodiments the promotion of angiogenesis promotes the growth of new blood vessels, while in some embodiments existing blood vessels are promoted to grow. Angiogenesis is a term well understood by those of ordinary skill in the art. In some embodiments endothelial survival refers to the process of preventing endothelial cells from dying. In some embodiments endothelial survival refers to the promoting the growth of endothelial cells.

In some embodiments "maintaining vascular integrity" refers to the process by which the a vascular system viability and functions are kept at specific level. In some embodiments the vascular system may be located throughout the individual. In some embodiments the vascular system may be localized to a specific region of the individual. For example, if a person has a poor vascular system in the foot, the pharmaceutical composition may be administered in a therapeutically effective amount to promote and maintain vascular integrity in that foot, while the rest of the vascular system may be unaffected. However, in other embodiments a therapeutically effective amount may promote angiogenesis, endothelial survival, and maintaining vascular integrity throughout the individual.

According to some embodiments, the present invention provides for methods for identifying compounds that modulates the binding of Ang-1 to ECM comprising performing a test assay that comprises the steps of contacting a protein that comprises at least an ECM-binding fragment of Ang-1 protein that comprises SEQ ID NO:1 and/or SEQ ID NO:2 with ECM material in the presence of a test compound and measuring the level of binding of the protein that comprises at least an ECM binding fragment of Ang-1 protein that comprises SEQ ID NO:1 and/or SEQ ID NO:2 with the ECM. In some embodiments the method further comprises comparing the level with the level of binding of the protein that comprises at least an ECM-binding fragment of Ang-1 protein that comprises SEQ ID NO:1 and/or SEQ ID NO:2 with ECM material in the absence of said test compound. In some embodiments when the level of binding of the protein that comprises at least an ECM-binding fragment of Ang-1 protein that comprises SEQ ID NO:1 and SEQ ID NO:2 with the ECM in the presence of the test compound is less than the level of binding of the protein that comprises at least an ECM-binding fragment of Ang-1 protein that comprises SEQ ID NO:1 and/or SEQ ID NO: 2 with the ECM in the absence of the test compound results indicate that the test compound modulates binding of Ang-1 to ECM by inhibiting the binding.

In some embodiments when the level of binding of the protein that comprises at least an ECM-binding fragment of Ang-1 protein that comprises SEQ ID NO:1 and/or SEQ ID NO: 2 with the ECM in the presence of the test compound is more than the level of binding of the protein that comprises at least an ECM-binding fragment of Ang-1 protein that comprises SEQ ID NO:1 and/or SEQ ID NO: 2 with the ECM in the absence of the test compound results indicate that the test compound modulates binding of Ang-1 to ECM by enhancing the binding.

As used herein, the term "modulates" refers to an increase or a decrease. In some embodiments the test compound increases the level of Ang-1 protein binding to the ECM. In some embodiments the test compound decreases the level of Ang-1 protein binding to the ECM.

As used herein, the term "at least an ECM-binding fragment of Ang-1 protein" refers to a protein that comprises a fragment of Ang-1 that can bind to ECM. In some embodiments this refers to SEQ ID NO:1 and/or SEQ ID NO:2. In other embodiments, this refers to protein that comprises a section of the protein that is homologous to an ECM-binding fragment of Ang-1 protein. In some embodiments, the protein can be the full-length Ang-1 protein or a fragment thereof. In some embodiments the "at least an ECM-binding fragment of Ang-1 protein" comprises SEQ ID NO:4, SEQ ID NO:6, and/or SEQ ID NO:8. In some embodiments, the protein can be a fusion protein that comprises Ang-1 protein sequence and non-Ang-1 protein sequence. In some embodiments, a protein comprising at least an ECM-binding fragment of Ang-1 protein comprises a peptide sequence that has at least 50%, at least 60%, at least 70%, at least 80%, at least 90%, at least 95%, at least 96%, at least 97%, at least 98%, at least 99%, at least 100% similarity to an ECM-binding fragment of Ang-1. In some embodiments a protein comprising at least an ECM-binding fragment of Ang-1 protein comprises a peptide sequence that has at least 50%, at least 60%, at least 70%, at least 80%, at least 90%, at least 95%, at least 96%, at least 97%, at least 98%, at least 99%, or at least 100% similarity to SEQ ID NO:4, SEQ ID NO:6, and/or SEQ ID NO:8. In some embodiments a protein comprising at least an ECM-binding fragment of Ang-1 protein comprises a peptide sequence that has at least 50%, at least 60%, at least 70%, at least 80%, at least 90%, at least 95%, at least 96%, at least 97%, at least 98%, at least 99%, or at least 100% similarity to SEQ ID NO:1 and/or SEQ ID NO:2.

According to some embodiments "ECM material" refers to a compound or material that is found in the extracellular matrix that can bind to an ECM-binding fragment of Ang-1 protein. According to some embodiments the "ECM material" refers to a composition comprising fibronection, laminin, type I collagen, type IV collagen, vitronectin, fibrinogen, matrigel, LLC carcinoma ECM, BSA, heparin, chondroitin sulfate, or hyaluronic acid.

In some embodiments the ECM material is produced by culturing cells on a substrate for a sufficient time for the cells to produce the ECM material on the substrate and then removing the cells from the substrate without removing the ECM material. In some embodiments the cells that are used to produce the ECM material are Lewis Lung carcinoma cells or TA3 murine mammary carcinoma cells. As used herein, the term "substrate" refers to any vessel or container that is capable of culturing cells. Examples of substrates include, but are not limited to, petri dishes, 6-well plates, 96-well plates, 384-well plates, and the like. Removing cells from the substrate without removing the ECM material is well within the skill of one of ordinary skill in the art. An example of how to remove the cells without removing the ECM includes contacting the cells with a chelator such as EDTA or EGTA for a sufficient time to remove the cells without effecting the ECM material. There are other methods that can performed the same function as contacting the cells with EDTA or EGTA and are within the scope of the current invention.

According to some embodiments the protein that comprises at least an ECM-binding fragment of Ang-1 comprising a detectable label. As used herein, the term "detectable label" refers to any molecule that can be detected with methods that are well known to those of ordinary skill in the art. Molecules with detectable labels include without limitation proteins, protein fragments, antibodies, fluorescent labels, radioactive labels, chromophores, chemilluminescent probes, and the like. In some embodiments the detectable label is used to measure the level of binding of the protein that comprises at least an ECM-binding fragment of Ang-1 protein on the ECM.

In some embodiments the method of identifying compound that modulates the binding of Ang-1 to ECM further comprises multiple test assays that are identical except that the amount of the test compound used differs. To aid in determining the effective amount of a test agent multiple assays are preformed using different amounts of the test compound. In some embodiments at least 2 assays are performed. In some other embodiments at least 3, at least 4, at least 5, at least 6, at least 7, at least 8, at least 9, at least 10, at least 15, at least 20, at least 30, at least 40, at least 50, at least 100 assays are performed using different amounts of the test compound.

According to some embodiments the methods of identifying a compound that modulates the binding of Ang-1 to ECM further comprises determining the level of binding of a protein that comprises at least an ECM-binding fragment of Ang-1 protein that comprises SEQ ID NO:1 and/or SEQ ID NO:2 with ECM material in the absence of the test compound by performing a control assay wherein the control assay comprises the steps of contacting a protein that comprises at least an ECM-binding fragment of Ang-1 protein that comprises SEQ ID NO:1 and/or SEQ ID NO:2 with ECM material in the absence of a test compound and measuring the level of binding of the protein that comprises at least an ECM binding fragment of Ang-1 protein that comprises SEQ ID NO:1 and/or SEQ ID NO:2 with the ECM.

Assays that can be used for the methods to identify compounds that modulates the binding of Ang-1 to ECM are well known to those of ordinary skill in the art and require only routine experimentation. Examples of assays that are well known to those of ordinary skill in the art include ELISA, Sandwich Assays, flow cytometry, immunoprecipitation, and the like.

According to some embodiments the present invention provides for pharmaceutical compositions comprising a pharmaceutically acceptable carrier and a therapeutically effective amount of Ang-2 protein and/or a vector comprising a nucleic acid molecule that comprises the nucleotide coding sequence of Ang-2.

As used herein, the term "Ang-2" refers to the protein or nucleic acid encoding the protein or fragment thereof of Angiopoietin-2. In some embodiments the Ang-2 is mammalian Ang-2. In some embodiments, the Ang-2 is human, mouse, rat, dog, cat, pig, or horse. In some embodiments the Ang-2 protein comprises SEQ ID NO:10 and/or SEQ ID NO:12. In some embodiments the Ang-2 nucleotide coding sequence comprises SEQ ID NO 9 and/or SEQ ID NO:11. In some embodiments, the Ang-2 protein or the nucleic acid that encodes Ang-2 is a fragment of the Ang-2 protein or the nucleotide coding sequence of Ang-2. In some embodiments the Ang-2 protein comprises a fragment of SEQ ID NO:10 and/or SEQ ID NO:12. In some embodiments, "Ang-2" refers to a fusion protein comprising non-Ang-2 protein sequence and Ang-2 protein sequence. According to some embodiments, "Ang-2" refers to a protein that has at least 50%, at least 60%, at least 70%, at least 80%, at least 90%, at least 95%, at least 96%, at least 97%, at least 98%, at least 99%, at least 100% similarity to SEQ ID NO:10 and/or SEQ ID NO:12. In some embodiments the nucleotide coding sequence comprises a nucleotide coding sequence that is at least 50%, at least 60%, at least 70%, at least 80%, at least 90%, at least 95%, at least 96%, at least 97%, at least 98%, at least 99%, at least 100% identical to SEQ ID NO:9 and/or SEQ ID NO:11.

According to some embodiments the present invention provides for methods of treating an individual, or an individual in need thereof, suspected of having cancer comprising the step of administering to the individual a pharmaceutical composition comprising a pharmaceutically acceptable carrier and a therapeutically effective amount of Ang-2 protein and/or a vector comprising a nucleic acid molecule that comprises the nucleotide coding sequence of Ang-2. The methods of administration are defined above as well as what is meant by a therapeutically effective amount.

The cancers that can be treated are not limited to any cancer described herein and can include cancers of the bladder, cancers of the brain, cancers of the breast, cancers of the colon, hodgkin's disease, cancers of the kidney, cancers of the lung, melanoma, non-hodgkin's lymphoma, oral cancer, ovarian cancer, prostate cancer, uterine/cervical cancer, leukemia, cancers of the pancreas, testicular cancer, solid tumors, and the like.

EXAMPLES

Angiopoietin-1 (Ang-1) and angiopoietin-2 (Ang-2) affect angiogenesis differently during embryogenesis and tumorigenesis. In an attempt to understand the molecular basis underlying the distinct roles of those two homologous molecules, we investigated the association of Ang-1 and Ang-2 with the extracellular matrix (ECM). TA3 murine mammary carcinoma (TA3) and Lewis lung carcinoma cells expressing v5 epitope-tagged Ang-1 and Ang-2 were used in our studies. The results indicated that Ang-1 is secreted and incorporated into the ECM of the tumor cells, whereas Ang-2 is not associated with the ECM. The mutagenesis study indicated the domain that is responsible for the ECM association of Ang-1 is the linker peptide region between the coiled-coil and the fibrinogen-like domains. A weak binding between the coiled-coil domain of Ang-1 and the ECM was observed. Immunocytochemistry study revealed a distinct ECM distribution pattern of Ang-1, which is quite different from that of fibronectin, laminin, and collagen types I and IV. The ECM-associated Ang-1 proteins are released, and Tie-2 receptors are phosphorylated upon the adhesion of human umbilical vein endothelial cells. Implications of the difference in the ECM association of Ang-1 and Ang-2, which are related to the regulation of angiopoietin activity and their roles in local versus distant angiogenesis during tumor metastasis, are discussed.

Ang-1 and -2 are expressed by tumor cells. We found that overexpression of exogenous Ang-2, but not Ang-1, inhibits growth and metastasis of Lewis lung carcinoma (LLC) and TA3 murine mammary carcinoma cells. The tumors overexpressing Ang-2 exhibited aberrant and incomplete angiogenesis in vivo, which is characterized by formation of the disorganized endothelial cell aggregates, the lack of endothelial associated smooth muscle cells, and massive apoptosis of the endothelial cells and surrounding tumor cells. This result is consistent with the notion that Ang-2 inhibits the Ang-1-dependent recruitment of smooth muscle cells.

To reveal the molecular basis underlying the different roles of angiopoietins in tumor angiogenesis, we investigated the relationship between angiopoietins and the ECM in the present study. We found that, unlike Ang-2, Ang-1 is secreted and incorporated into the ECM via its linker peptide region. The association between Ang-1 and the ECM is strong, and the distribution of Ang-1 in the ECM is unique and different from that of fibronectin, laminin, and collagen type I and type IV. The releasing or incorporation of Ang-1 from or into the ECM is regulated by different factors. Tie-2 phosphorylation was detected in HUVECs seeded onto the ECM containing Ang-1, which indicates a regulatory role of the ECM association of Ang-1 in tumor angiogenesis.

Ang-2 expression is regulated by hypoxia and growth factors. Unlike Ang-2, little is known about the regulation of Ang-1 expression. The finding reported herein offers a possible regulatory mechanism for the availability of Ang-1 proteins, that is instead of regulating the production of Ang-1, it may be regulated by its ECM association. The strong ECM binding of Ang-1 implies the effect of Ang-1 is limited to the local environment where it is produced, whereas Ang-2 can diffuse to and affect angiogenesis in the distant sites.

Experimental Procedures

Cell Culture and Reagents—Lewis lung carcinoma (LLC, ATCC), TA3 mammary carcinoma (37) cells, and the tumor cell transfectants were maintained as described (17). Anti-laminin, -fibronectin (Sigma), -collagen types I and IV (Biodesign international), -phosphotyrosine (PY20, Calbiochem), -Tie-2 (C-20, Santa Cruz Biotechnology), -Ang-1 (C-19, Santa Cruz Biotechnology), and -v5 antibodies were used.

Construction of the Expression Vectors—Full-length Ang-1 and Ang-2 cDNAs were generated by RT-PCR as described (17, 40). The coiled-coil domain and the coiled-coil plus the linker peptide region were generated by RT-PCR using the following pairs of primers. The forward primer for the coiled-coil domain is 5'-ACAATGACAGTTTTC-CTTTCCTTT-3' (SEQ ID NO: 13) and the reverse primer is 5'-TGTGTCCATGAGCTCCAGTTGTTG-3' (SEQ ID NO: 14). The coiled-coil plus the linker peptide region was amplified using the same forward primer as that of the coiled-coil domain and a reverse primer, 5'-AAATGGTTTCTCTTCT-TCTCTTTT-3' (SEQ ID NO: 15). The stop codons were omitted from the reverse primers so that the v5 and 6× histidine tags in the pEF6/V5-His expression vector (Invitrogen) can be attached to the C terminus of the Ang-1 fragments. To fuse the FHD of Ang-1 to the signal peptide of Ang-1, we used the full-length Ang-1 in the expression vector (17) as a template and the ExSite PCR-based site-directed mutagenesis kit (Stratagene) together with a forward primer derived from the beginning of the FHD, 5'-CGAGACTGTGCAGATGTATAT-CAA-3' (SEQ ID NO: 16), and a reverse primer derived from the end of the signal peptide, 5'-TCTTCTCCCTC-CGTTTTCTGGATT-3' (SEQ ID NO: 17). The extracellular domain of Tie-2 was obtained by RT-PCR using the following pair of primers. The forward primer is 5'-AGTATG-GACTCTTTAGCCGGCTTA-3' (SEQ ID NO: 18) and the reverse primer is 5'-CATCTTTCCCCCTCCGAGGTCTGC-3' (SEQ ID NO: 19). The PCR products were inserted in frame into 5'-end of the Fc fragments of human IgG in pEF6/V5-His expression vectors to generate the Tie-2-Fc fusion construct (40). The authenticity and orientation of the cDNA inserts were confirmed by DNA sequencing.

Transfection—LLC and TA3 carcinoma cells were transfected with the expression constructs containing Ang-1, Ang-2, or the expression vector alone. The transfected cells expressing Ang-1 and Ang-2 were identified as described (17). COS-7 cells were used in the transient transfection of Ang-1 and -2, the coiled-coil domain, the coiled-coil plus linker region, and the FHD of Ang-1 using LipofectAMINE (Life Technologies, Inc.) as described (17).

Preparation of the Secreted and the ECM-Associated Proteins and Western Blot Analysis—The cell culture supernatants of LLC and TA3 transfectants or the transiently transfected COS-7 cells were collected. The confluent cells layers were released from the culture dishes by incubating with PBS containing 5 mM EDTA. The ECM components remaining on the culture dishes were washed and extracted with 1×SDS Laemmli sample buffer with or without 5%-mercaptoethanol.

To determine the affinity of the ECM association of Ang-1, the confluent LLC cells expressing Ang-1 were lifted as described. The remaining ECM components were extracted with 0.5 M PBS and 1 M sodium chloride (NaCl) and 0.5 and 1% deoxycholate (DOC) at room temperature for 10 min. The remaining insoluble materials were solubilized by 1×SDS Laemmli sample buffer and subjected to Western blot analysis.

Immuocytochemistry—LLC cells expressing Ang-1 or Ang-2 or transfected with the expression vectors were cultured in 35-mm dishes until subconfluence or confluence. They were fixed with methanol at 20° C. for 15 min. Antibodies against v5 epitope, fibronectin, laminin, type I or IV collagens were used to detected Ang-1v5, Ang-2v5, fibronectin, laminin, types I or IV collagen, respectively, in those fixed cells.

Extraction of the ECM Components and Affinity Purification—The ECM materials derived from the cultured LLC cells were extracted overnight at 4° C. in 2 M urea and 0.05 M Tris-HCl (pH 7.4). The soluble materials were dialyzed against PBS and used to coat the enzyme-linked immunosorbent assay plates. The ECM derived from the LLC transfectants expressing Ang-1 was extracted in the same way. The ECM extracts containing Ang-1 proteins and the serum-free culture media containing secreted Ang-2, both of which contain v5 and 6× histidine tags at their C-terminal ends, were loaded onto Ni+ Probond affinity columns (Invitrogen) and purified following the manufacturer's instructions.

Purified Ang-1v5/His proteins were loaded onto a heparin-Sepharose CL-6B column to test their affinity to heparin. The flow-through fraction was collected, and the column was washed with different concentrations of NaCl from 0.15 to 1 M. The eluted fractions were collected and, along with the flow-through fractions, were subjected to Western blot analysis.

Solid Phase Binding Assay—96-Well enzyme-linked immunosorbent assay plates were coated overnight at 4° C. with different ECM components. The components were fibronectin, laminin, type I and IV collagens, Matrigel (20 µg/ml, Becton Dickinson), vitronectin (10 µg/ml, Sigma), fibrinogen (20 µg/ml, Sigma), heparin, chondroitin sulfate, hyaluronic acid (200 µg/ml, Sigma), and the whole ECM extracts derived from LLC cells (100 µg/ml). The coated plates were washed and blocked with 0.5% bovine serum albumin. The affinity-purified Ang-1v5/His and Ang-2v5/His were added into the coated plates (100 ng/ml) for overnight incubation at 4° C. After extensive washing, the bound Ang-1 and Ang-2 were detected. The assays were performed in triplicate.

Tie-2 Tyrosine Phosphorylation Assay—LLC carcinoma cells expressing Ang-1 or Ang-2 were cultured in 100-mm dishes until confluence and were lifted from the dishes as described. The dishes containing the ECM components deposited by the cultured cells were used immediately.

HUVECs (ATCC) were cultured until subconfluence, and switched into the serum-free medium overnight. The cells were then lifted with 0.53 mM EDTA in Hanks' balanced buffer (Life Technologies, Inc.) and washed. 1×106 HUVECs were seeded onto a plastic dish or one of the ECM-coated dishes freshly generated as described above. They were cultured at 37° C. in serum-free medium with or without soluble Ang-1 (200 ng/ml) or Tie-2-Fc fusion proteins (2 µg/ml) for 30 min. The cells were then lysed at 4° C. with the lysis buffer (50 mM Tris-HCl (pH 7.4), 50 mM NaCl, 1% Triton X-100, 2 mM EDTA, 2 mM sodium orthovanadate, 2 mM sodium fluoride, 2 mM phenylmethylsulfonyl fluoride, 1 mM leupeptin, 1 mM pepstatin A, and 10 µg/ml aprotinin). Tie-2 proteins were immunoprecipitated using anti-Tie-2 polyclonal antibody (Santa Cruz Biotechnology). The immunoprecipitated proteins were subjected Western blot analysis using anti-phosphotyrosine antibody (Y20, Calbiochem).

Results

Angiopoietin-1, but not Angiopoietin-2, Binds to the Extracellular Matrix—In the process of studying the role of angiopoietins in tumor angiogenesis, we experienced difficulty obtaining the transfected tumor cells that secrete high levels of Ang-1, whereas the transfectants that secrete high levels of Ang-2 were easily obtained. One possible reason for the phenomena is that Ang-1 and Ang-2 may associate with the ECM differently. To investigate that, we generated the stably transfected Lewis lung carcinoma (LLC) and TA3 murine mammary carcinoma (TA3) cells expressing v5 epitope-tagged Ang-1 or Ang-2 (FIG. 1, A, a and b). Under non-reducing conditions both Ang-1 and Ang-2 tend to aggregate with each other to form dimers and oligomers (FIG. 1, A and B). The patterns of the aggregation are distinct between Ang-1 and Ang-2. Ang-1 tends to form higher order oligomers (FIG. 1A), whereas Ang-2 forms dimers, trimers, and oligomers. The molecular weight of the monomer of Ang-1 and Ang-2 is ~70 kDa. Because of the C-terminal v5 and 6× histidine epitope tags, Ang-1v5 and Ang-2v5 migrate a little slower.

The aggregation of Ang-1 and Ang-2 is sensitive to the reducing agents, such as—mercaptoethanol. After boiling the protein samples in 1× Laemmli SDS sample buffer containing 5%-mercaptoethanol, the aggregated Ang-1 and Ang-2 are dissociated into monomers (data not shown). It was noted that the amount of the secreted Ang-1 is often lower than that of Ang-2 derived from LLC and TA3 transfectants (FIG. 1A, a and b). To examine the possibility that the lack of Ang-1 secretion is due to incorporation of Ang-1 into the ECM of the tumor cells, the transfectants expressing Ang-1 and Ang-2 were grown until confluence, and the cells were then detached from the culture dishes by the EDTA treatment, which is a standard procedure to release cultured cells and leave the ECM components behind on the culture dishes (38). The remaining ECM components were then extracted from the culture dishes by 1×SDS Laemmli buffer with or without -mercaptoethanol. Western blot analyses were performed using anti-v5 monoclonal antibody to detect v5-tagged Ang-1 or Ang-2. The results indicated that Ang-1 is present in the ECM fraction of the transfected tumor cells, whereas Ang-2 is absent (FIG. 1B). The ECM-associated Ang-1 is highly aggregated to form oligomers, and no monomer is detected (FIG. 1B, lanes 1 and 2, and 6 and 7). The aggregated Ang-1 oligomers were dissociated into the monomers by the treatment with -mercaptoethanol (FIG. 1C), which indicates the role of the cysteine residues in the aggregations. Thus, we have established that Ang-1, but not Ang-2, is incorporated into the ECM of those carcinoma cells.

To confirm that the endogenously expressed Ang-1 is associated with the ECM as the transfected Ang-1, the polyclonal anti-Ang-1 antibody (C19, Santa Cruz Biotechnology) was first purified through an Ang-1v5-conjugated protein A affinity column. The purified antibody was used in Western blot analysis of the ECM components derived from HUVECs. The results indicated that Ang-1 produced by HUVECs is incorporated into the ECM (data not shown). Due to the superior quality of the anti-v5 monoclonal antibody compared with that of the polyclonal anti-Ang-1 antibody, even after the affinity purification (Santa Cruz Biotechnology), most of the following experiments were performed using the transfected tumor cells expressing v5-tagged Ang-1 and Ang-2.

Figure 2:
FIG. 2 shows data related to the ECM association of angiopoietin-1. The Ang-1-containing ECM was extracted at room temperature for 10 min with 0.15, 0.5, and 1 M NaCl and 0.5 and 1% DOC, respectively. The insoluble ECM components were then extracted with 1×SDS Laemmli buffer and subjected to Western blot analysis using anti-v5 antibody (lanes 2-6, respectively). The proteins in the lane 1 were derived from the ECM without prior extraction with any reagents. Lanes 7 and 8 are the ECM extracts derived from LLC cells expressing Ang-2 or transfected with the expression vector alone, respectively. The molecular mass markers are as indicated.

The Biochemical Characters of the ECM-associated Ang-1—The strength of the ECM association of Ang-1 was tested by extracting the cell-free ECM deposited on the culture dishes by LLC cells expressing Ang-1v5 with different concentrations of sodium chloride (NaCl) and deoxycholate (DOC). The insoluble materials after the extractions were solubilized with 1×SDS Laemmli buffer and subjected to Western blot analysis. As shown in FIG. 2, most of the ECM-incorporated Ang-1 resisted 0.15 M NaCl extraction (FIG. 2, lane 2); a fair amount of Ang-1 remains in the ECM after 1 M NaCl extraction (FIG. 2, lane 4), and a fraction of Ang-1 is in the ECM fraction even after 1% DOC extraction (FIG. 2, lane 6), which indicated a strong ECM association and implicated a gradual assembly process of Ang-1 into the ECM (FIG. 2).

Figure 3:
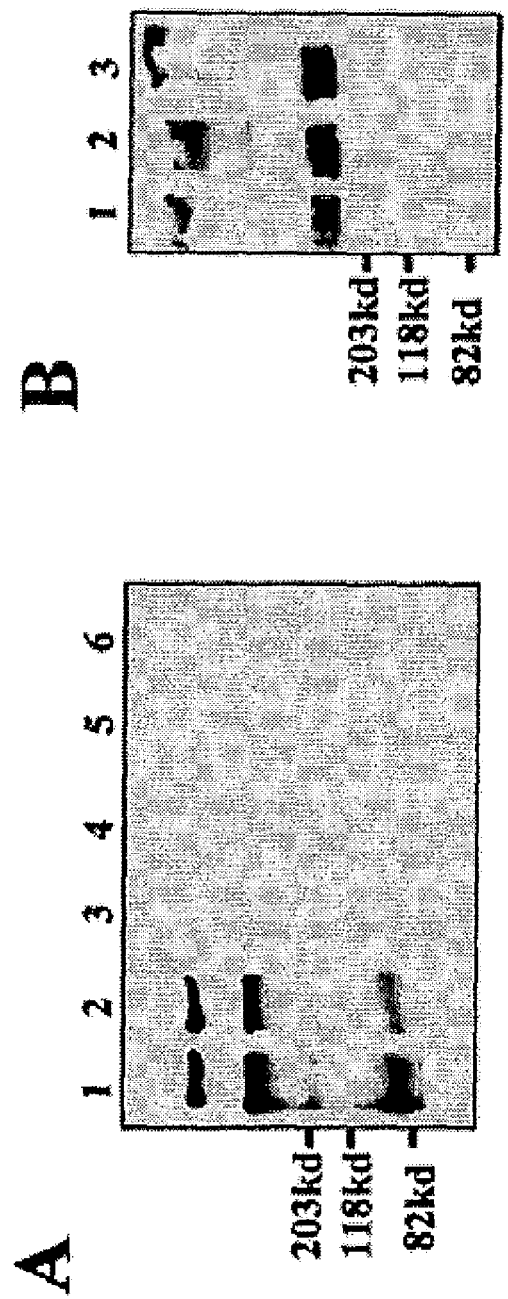
FIGS. 3A and 3B show data demonstrating Ang-1 does not bind to heparin.

The Binding Affinity of Ang-1 to Different ECM Components—The C terminus of Ang-1 shares the sequence homology with fibrinogen, which binds to heparin. To investigate whether Ang-1 binds to the ECM via its interaction with the sulfated glycosaminoglycans, the purified Ang-1v5/His (FIG. 3A, lane 1) was applied to a heparin-Sepharose CL-6B affinity column (Amersham Pharmacia Biotech). The unbound flow-through was collected, and the column was washed with 0.15, 0.3, 0.5, 1 M NaCl (FIG. 3A, lanes 3-6). The eluted fractions were collected, and along with the flow-through fraction, they were subjected to the Western blot analysis by using anti-v5 monoclonal antibody to detect the presence of Ang-1v5/His in each fraction. The results indicated that Ang-1v5/His does not bind to the heparin affinity column and was fully recovered in the flow-through fraction (FIG. 3A, lane 2). To confirm the above finding and avoid the possibility that the purified soluble Ang-1v5/His may be modified and different from the ECM-associated Ang-1 and thereby unable to bind to heparin, soluble sulfated glycosaminoglycans, heparin, and chondroitin sulfate (200 µg/ml) were added into serum-free cell culture medium (SFM) of LLC carcinoma cells expressing Ang-1. After 2, 12, and 24 h of incubation, the SFM and ECM fractions were collected and analyzed. The Western blot results indicated that neither heparin nor chondroitin sulfate releases Ang-1 from the ECM of the transfected LLC cells (FIG. 3B, and data not shown).

Figure 4:
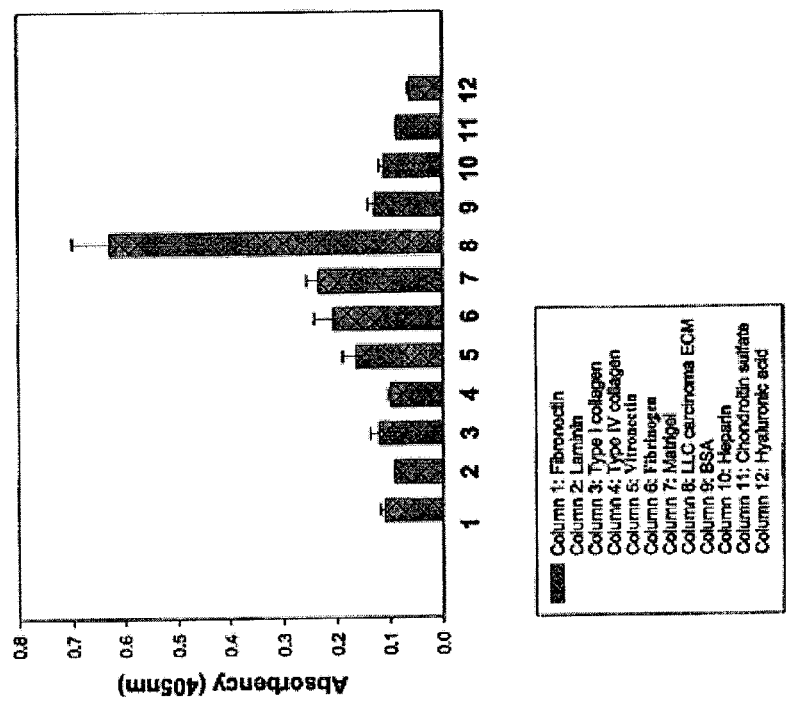
FIG. 4 shows binding of Ang-1 to the different ECM components. The binding affinities of Ang-1 to several different ECM components were determined in the solid phase binding assays. Ang-1 exhibited no affinity to fibronectin, laminin, collagen types I and IV (columns 1-4, respectively), heparin, chondroitin sulfate, and hyaluronic acid (columns 10 and 12, respectively). The weak affinities of Ang-1 to vitronectin and fibrinogen were observed (columns 5 and 6). Ang-1 displayed a moderate affinity to Matrigel (column 7) and a strong affinity to the 2 M urea ECM extracts derived from LLC carcinoma cells (column 8). All the experiments were performed in triplicate.

In an attempt to identify the ECM component(s) that bind(s) to Ang-1, solid phase binding assays were performed to assess the binding affinity of Ang-1 to several ECM components. The assays were performed in triplicate, and the results are listed in the FIG. 4. The purified Ang-1v5 binds to whole ECM extracts derived from LLC carcinoma cells with high affinity (FIG. 4, column 8). The weak bindings to Matrigel, fibrinogen, and vitronectin were observed, which can't account entirely for the high affinity binding between Ang-1 and the ECM extracts. Ang-1 displayed no affinity to fibronectin, laminin, collagen type I and type IV, heparin, chondroitin sulfate, and hyaluronic acid (FIG. 4). This result offered the possibility that Ang-1 binds to the ECM via an unidentified ECM protein(s).

Figure 5:
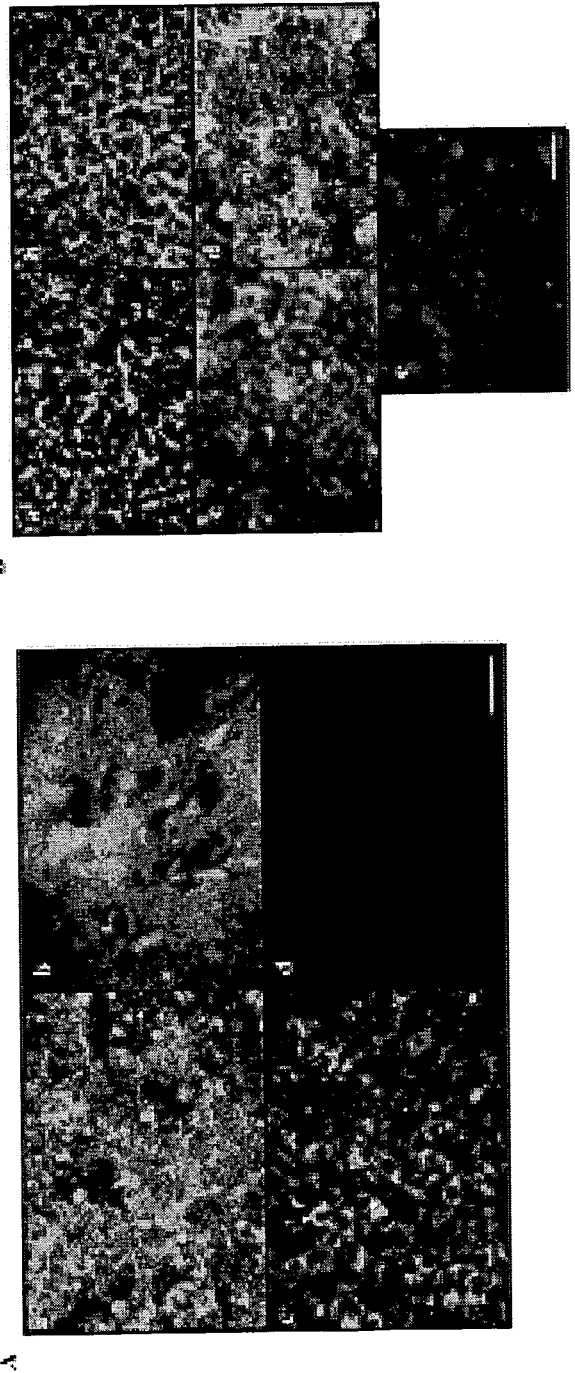
FIGS. 5Aa, 5Ab, 5Ac, 5Ad, 5Ba, 5Bb, 5Bc, 5Bd and 5Be show Ang-1 displayed a distinct ECM distribution pattern. The distribution of Ang-1 in LLC cells expressing Ang-1v5 was investigated by immunocytochemistry using anti-v5 antibody (FIG. 5Aa). The distribution was compared with that of fibronectin (FIG. 5Ba), laminin (FIG. 5Bb), collagen type I (FIG. 5Bc) and type IV (FIG. 5Bd), and Ang-2 in LLC cells expressing Ang-2v5 (FIG. 5Ac). The cell-free ECM derived from the LLC carcinoma cells expressing Ang-1 (FIG. 5Ab) or Ang-2 (FIG. 5Ad) was also analyzed by immunocytochemistry using anti-v5 antibody. LLC carcinoma cells stained with the FITC-conjugated rabbit anti-mouse secondary antibody only are shown in FIG. 5Be. Bar, 40 µm.

Immunocytochemistry Studies Revealed a Distinct ECM Distribution Pattern of Angiopoietin-1—The distribution patterns of Ang-1 and Ang-2 were investigated and compared with fibronectin, laminin, and type I and IV collagens by performing immunocytochemistry on LLC carcinoma cells expressing Ang-1v5 or Ang-2v5 using anti-v5 antibody or antibodies against the appropriate ECM proteins. The cell-free ECM deposited by LLC cells expressing Ang-1 or Ang-2 was also examined. The immunocytochemistry studies uncovered a distinct Ang-1 distribution pattern in the ECM of LLC carcinoma cells, which is different from the distribution of fibronectin, laminin, and types I and IV collagen (FIGS. 5, A and B). Ang-1 is incorporated into the ECM as small granule-like depositions, which are more or less evenly distributed beneath the cells (FIGS. 5A, a and b). Some cell-free spaces, which are left behind by the migrating cells, are positive for the similar Ang-1 depositions (FIG. 5A, a, arrow). The distribution pattern of Ang-1 was preserved even after the cells were lifted by the treatment of EDTA (FIG. 5A, b), which indicated that instead of loosely binding to the tumor cells, those Ang-1 proteins are incorporated into the ECM of the tumor cells. On the contrary, there is no trace of Ang-2 in the cell-free ECM deposited by the cells expressing Ang-2 (FIG. 5A, d). Ang-2 was only detected in the cytoplasm of the transfected cells, which presumably reflects the presence of Ang-2 in the secretory pathway of the cells (FIG. 5A, c, arrowheads).

Figure 6:
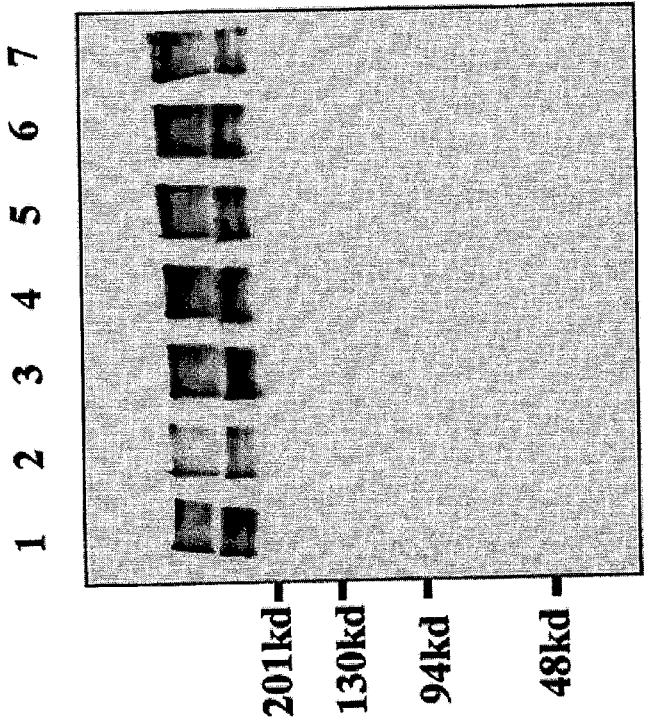
FIG. 6 shows ECM-associated Ang-1 is released in the response to PMA stimulation. Several factors were tested for their abilities to release the ECM-sequestered Ang-1. After the incubation of the LLC carcinoma cells expressing Ang-1 with SFM alone (lane 1) or SFM containing PMA (0.5 µg/ml, lane 2), TGF-1 (0.5 ng/ml, lane 3), bFGF (1 ng/ml, lane 4), epidermal growth factor (10 ng/ml, lane 5), heparin-binding epidermal growth factor (10 ng/ml, lane 6), and TGF-2 (0.5 ng/ml, lane 7), respectively, for 14 h, the cells were released from the cell culture dishes by the treatment of EDTA, and the remaining ECM components were extracted with 1×SDS Laemmli buffer and subjected to the Western blot analysis using anti-v5 antibody. Molecular mass markers are as indicated.

Angiopoietin-1 Is Released in the Response to Phorbol 12-Myristate 13-Acetate (PMA)—The association of Ang-1 with the ECM of tumor cells led us to explore the regulatory mechanisms of its incorporation and releasing, which may modulate its activity. The confluent LLC carcinoma cells expressing Ang-1 were cultured overnight in the presence of different growth factors or PMA in serum-free cell culture medium. After releasing the cells from the culture dishes, the remaining ECM components were extracted with 1×SDS Laemmli buffer and subjected to Western blot analysis using anti-v5 antibody. The results indicated that PMA stimulates the releasing of the ECM-associated Ang-1 (FIG. 6, lane 2). Transforming growth factor-1 (TGF-1) promotes slightly the incorporation of Ang-1 into the ECM, which may reflect the positive effect of TGF-1 on synthesis of the ECM components (FIG. 6, lane 3).

Figure 7:
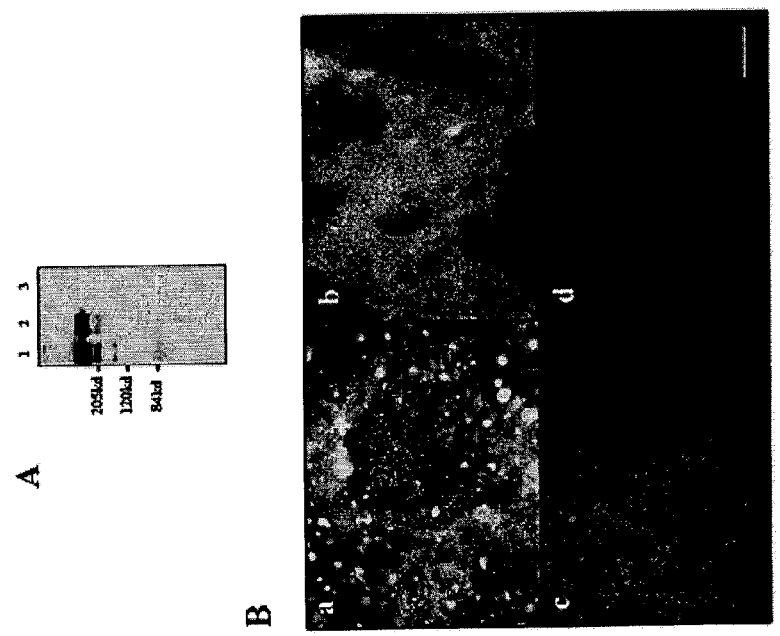
FIGS. 7A, 7Ba, 7Bb, 7Bc and 7Bd shows ECM-associated Ang-1 exhibited no affinity to Tie-2-Fc fusion protein. A, Tie-2-Fc fusion protein is capable of precipitating Ang-1 proteins from the protein extracts, which were derived from the 2 M urea extraction of the ECM of LLC carcinoma cells expressing Ang-1 (A, lane 2). The starting materials for the immunoprecipitation were loaded in lane 1 (A), and the control for the immunoprecipitation contains everything except Tie-2-Fc fusion proteins (A, lane 3). Molecular mass markers are as indicated. B, the LLC cells expressing Ang-1 or the ECM derived from LLC carcinoma cells expressing Ang-1 were incubated with Tie-2-Fc fusion proteins (B, c and d) or anti-v5 antibody (B, a and b), and FITC-conjugated rabbit anti-human Fc or anti-mouse secondary antibodies were used, respectively. Bar, 30 µm.

The ECM-associated Ang-1 Does Not Bind to Tie-2-Fc Fusion Protein—To determine whether the ECM-associated Ang-1 proteins bind to Tie-2-Fc fusion proteins, the confluent LLC cells expressing Ang-1 or the ECM deposited by the LLC cells expressing Ang-1 were fixed and incubated with anti-v5 antibody or the purified Tie-2-Fc fusion proteins. Anti-v5 antibody and FITC-conjugated rabbit anti-mouse antibody (Sigma) revealed that many Ang-1 proteins were deposited into the ECM of the tumor cells (FIG. 7B, a and b); however, Ang-1 proteins in the ECM exhibited no affinity to Tie-2-Fc fusion proteins (FIG. 7B, c and d). In order to eliminate the possibility that the fixation procedure could affect the binding between the ECM-associated Ang-1 and Tie-2-Fc fusion protein, Tie-2-Fc fusion proteins were directly added into the cultured LLC carcinoma cells expressing Ang-1 or into the ECM freshly derived from the LLC cells expressing Ang-1. No binding was detected in both cases (data not shown). Those ECM-associated Ang-1 proteins were extracted by 2 M urea/Tris-HCl buffer (pH 7.4), dialyzed in PBS, and immunoprecipitated using Tie-2-Fc fusion proteins and protein A beads. The precipitated proteins were subjected to Western blot analysis using anti-v5 antibody. Ang-1 proteins were found to be precipitated by Tie-2-Fc fusion proteins (FIG. 7A, lane 2). Together, those results suggested that after their secretion from the tumor cells, Ang-1 proteins are incorporated into the ECM, and their Tie-2-binding sites are no longer accessible; upon the release from the ECM, the solubilized Ang-1 proteins regained their ability to bind to Tie-2. Under physiologic conditions, this may serve as an efficient regulatory mechanism for Ang-1 activity.

Figure 8:
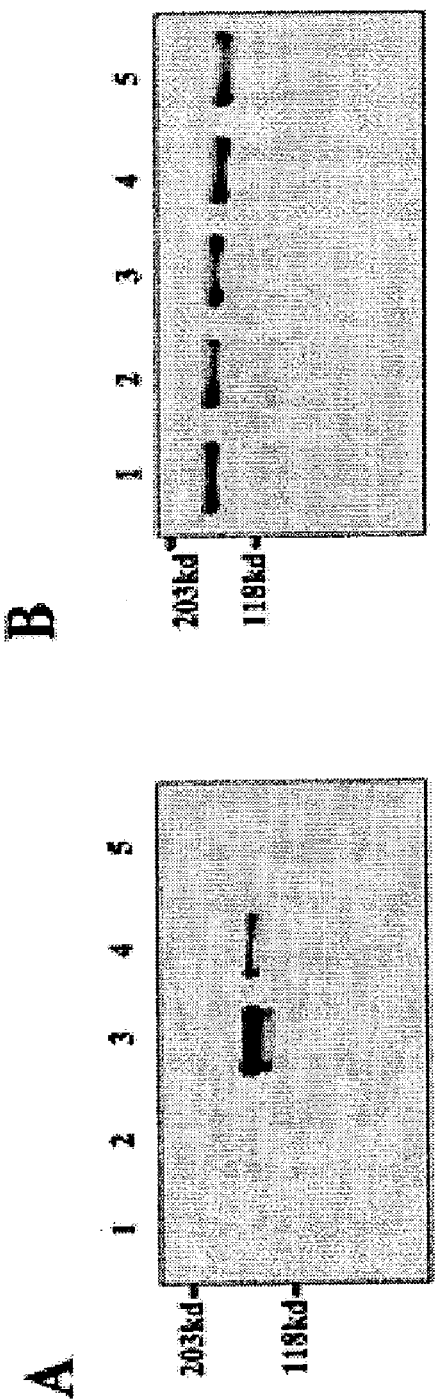
FIGS. 8A and 8B show Tie-2 receptors on HUVECs phosphorylated upon the adherence of HUVECs to the Ang-1-containing ECM. The serum-starved HUVECs were lifted by the treatment of EDTA/Hanks' balanced salt solution, and 1×106 of the HUVECs were seeded into the plastic dish containing SFM with (200 ng/ml, lane 3) or without soluble Ang-1 (lane 1) or the dishes coated with the ECM derived from LLC cells expressing Ang-2 (lane 2) or Ang-1 in the presence (lane 5, 2 µg/ml) or absence of Tie-2-Fc fusion proteins (lane 4) for 30 min. The HUVECs were lysed, and 50 µg of proteins from each lysate were subjected to Western blot analysis using anti-Tie-2 antibody (Santa Cruz Biotechnology, FIG. 8B). The rest of the proteins were used in the immunoprecipitation using anti-Tie-2 antibody (Santa Cruz Biotechnology). The immunoprecipitated proteins were subjected to Western blot analysis using anti-phosphotyrosine (FIG. 8A). Molecular mass markers are as indicated.

Tie-2 Phosphorylation Is Achieved by Adhering HUVECs to the ECM Containing Ang-1 Proteins—To study whether the ECM-associated Ang-1 plays a role in angiogenesis, the ability of the ECM-associated Ang-1 to promote Tie-2 receptor phosphorylation was evaluated using HUVECs. The subconfluent HUVECs were serum-starved for about 14 h and then lifted from the culture dishes. 1×106 cells were seeded onto a plastic culture dish with (FIG. 8, lane 3) or without (FIG. 8, lane 1) purified soluble Ang-1 (200 ng/ml) or the culture dish containing the ECM components deposited by the confluent LLC cells expressing Ang-1 (FIG. 8, lane 4) or Ang-2 (FIG. 8, lane 2). The HUVECs were incubated on those cell culture dishes for 30 min and then lysed at 4° C. with the lysis buffer. The amount of the Tie-2 proteins in the lysates was determined by Western blot analysis of 50 µg of proteins from each lysate using anti-Tie-2 antibody (C-20, Santa Cruz Biotechnology, FIG. 8B). The results indicated that the endothelial cells used in the experiments express a similar amount of Tie-2 receptors (FIG. 8B). The phosphorylated Tie-2 proteins in the lysates were assessed by performing immunoprecipitation using anti-Tie-2 polyclonal antibody (C-20, Santa Cruz Biotechnology) and analyzing the precipitated proteins on Western blot using anti-phosphotyrosine antibody (Y20, Calbiochem). The results indicated that Tie-2 receptors on HUVECs are phosphorylated by Ang-1 derived from the ECM, and the phosphorylation is inhibited by the addition of the excess amount of Tie-2-Fc fusion proteins (2 µg, FIG. 8, lane 5).

To assess whether HUVECs release Ang-1 proteins from the ECM, HUVECs cells (1×106 cells/100-mm dish) or the serum-free culture media (SFM) alone were placed on the ECM deposited by LLC cells expressing Ang-1 for 30 min. The cell culture dishes with or without HUVECs were treated with 5 mM EDTA in PBS for 5 min to release the adhering cells. The remaining ECM materials on the culture dishes were extracted and subjected to Western blot analysis, and the results indicated that the reduced amount of Ang-1 is retained in the ECM after the adhesion of HUVECs compared with that retained in the ECM incubated with SFM alone (data not shown). Thus, HUVECs promote the release of Ang-1 from the ECM.

Figure 9:
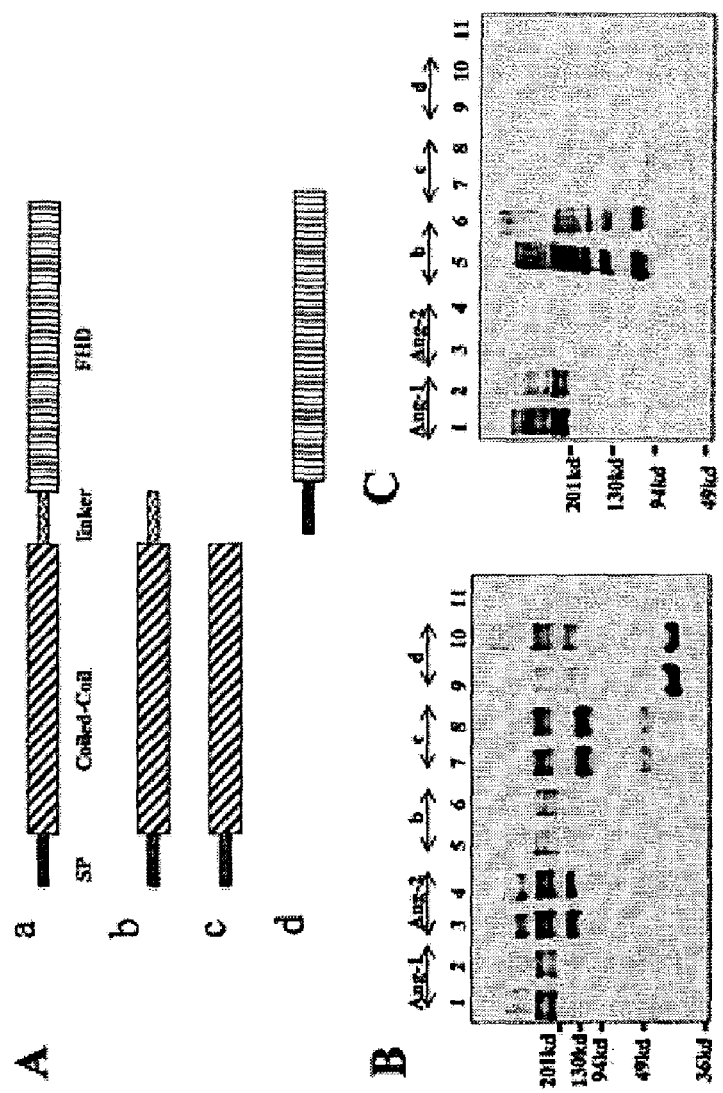
FIGS. 9Aa, 9Ab, 9Ac, 9Ad, 9B and 9C show the linker peptide region of Ang-1 is responsible for its ECM association. Several cDNA expression constructs were made including the full-length of Ang-1 or Ang-2, the coiled-coil region, the coiled-coil plus the linker peptide region, the fibrinogen-like region of Ang-1 (FIGS. 9Aa, 9Ab, 9Ac, 9Ad). All the Ang-1 fragments contain N-terminal signal peptides of Ang-1 and the C-terminal v5 epitope tags. These expression constructs were used to transfect COS-7 cells transiently. 72 h after the transfection, the cell culture supernatants (FIG. 9B) and the ECM proteins (FIG. 9C) were collected or extracted and subjected to Western blot analyses to determine the distribution of Ang-1, Ang-2, and the Ang-1 fragments using anti-v5 antibody. Lanes 1 and 2, full-length Ang-1; lanes 3 and 4, full-length Ang-2; lanes 5 and 6, the coiled-coil domain plus the linker peptide region of Ang-1; lanes 7 and 8, the coiled and coil region of Ang-1; lanes 9 and 10, the fibrinogen homology domain of Ang-1; lane 11, COS-7 cells transfected with the expression vector alone. Molecular mass markers are as indicated.

The Domain That Mediates the ECM Binding of Ang-1 Is Mapped to Its Linker Peptide Region—To determine which domain of Ang-1 mediates its ECM association, several expression constructs were made as indicated in FIG. 9A. They were the coiled-coil domain, the coiled-coil plus linker peptide region, and the FHD of Ang-1. The cDNA sequence encoding the signal peptide of Ang-1 was constructed into the N terminus of the above cDNA fragments so those fragments can be secreted properly (FIG. 9A). The full-length Ang-1 and -2 and the fragments of Ang-1, which contain C-terminal v5 epitope tags, were used to transfect COS-7 cells. 72 h after the transient transfection, the cell culture supernatants and the ECM materials derived from the transfected cells were either collected or extracted from the cell culture dishes and subjected to Western blot analyses using anti-v5 antibody to determine the distribution patterns of Ang-1, Ang-2, and the different fragments of Ang-1. The results indicated that the linker peptide region of Ang-1 between the coiled-coil and the fibrinogen-like domains, which contains 27 amino acids, is mainly responsible for the ECM association of Ang-1 (FIG. 9, B and C, lanes 5 and 6). A weak interaction between the coiled-coil domain of Ang-1 and the ECM was also detected (FIG. 9, B and C, lanes 7 and 8).

To investigate whether the ECM binding domain in the linker peptide region of Ang-1 is also present in Ang-2, we first compared the sequence homology between the domains of Ang-1 and Ang-2. We found that the percentages of the identical amino acids are 59, 19, and 64%, respectively, in the coiled-coil domain, the linker peptide region, and the fibrinogen-like domains of Ang-1 and Ang-2. No significant homology in the linker peptide region implied that the ECM binding domain in this region of Ang-1 is likely absent in the Ang-2 molecule.

To confirm that the absence of the ECM binding of Ang-2 is due to the lack of the ECM-binding site(s) in the molecule, but not the blockage of the binding site(s) by possible steric restraints in the full-length Ang-2 molecule, we made three additional deletions of Ang-2, which are similar to those of Ang-1 deletions (FIG. 9A). They are the coiled-coil domain, the coiled-coil plus the linker peptide region, and the fibrinogen-like domain of Ang-2. All the deletion constructs contain the N-terminal signal peptides of Ang-2 for their proper expression and secretion and the C-terminal v5 epitope tags derived from the pEF/6/v5-His expression vectors for their detection. After confirming the authenticities of the expression constructs by DNA sequencing, they were used to transfect COS-7 cells. After the transient transfection, the distributions of Ang-2 fragments in the cell culture media and the ECM fractions were examined by Western blot analysis. Our results indicated that all three fragments of Ang-2, the coiled-coil domain, the coiled-coil plus the linker peptide region, and the fibrinogen-like domain, are secreted as the full-length Ang-2; none of them associates with the ECM of the transfected COS-7 (data not shown). This result indicated clearly that unlike Ang-1, Ang-2 does not contain the ECM binding domain.

Discussion

Studies have shown that angiopoietin-1 and -2 are unique antagonists. Ang-2 blocks tyrosine phosphorylation of Tie-2 induced by Ang-1 and disrupts angiogenesis in vivo. Ang-1 and -2 play different roles in tumor angiogenesis. Ang-2 inhibits tumor angiogenesis by blocking recruitment of smooth muscle cells to the newly formed blood vessels and causing apoptosis to the endothelial cells.

Functional Significance of the ECM Association of Ang-1—In this study, we examined the potential relationship of Ang-1 and -2 with the ECM, which is known to modulate activities of many growth factors, including VEGF and bFGF. Our results indicated that unlike Ang-2, Ang-1 is secreted and incorporated into and sequestered by the ECM. The different ECM association capacity enables those two antagonists to regulate local and distant angiogenesis differently. Ang-1 is most likely to regulate angiogenesis in the vicinity of its secretion sites, whereas Ang-2 is likely to diffuse through interstitial tissues and blood vessels to the distant organs.

The ability to distribute Ang-1 and -2 to local environment and/or distant sites may play an important role in regulating tumor dormancy in some situations. Both Ang-1 and -2 are expressed by endothelial and tumor cells. During the growth of primary tumors, balanced expression of local Ang-1 and -2 and expression of other pro-angiogenic factors, such as VEGF, may ensure tumor angiogenesis and growth in the primary sites. When Tie-2 receptors on local endothelial cells are saturated, it is likely that the excess amount of Ang-1 produced by the primary tumors would be incorporated into and sequestered by the surrounding ECM, whereas the excessive amount of Ang-2 may diffuse to distant organs. The micrometastases seeded and developed in the distant organs, such as lung and liver, have microenvironments that contain pro- and anti-angiogenic factors produced by local micrometastatic tumors and surrounding host stromal tissues and are more or less similar to the microenvironments of primary tumors. However, on top of the microenvironments, Ang-2, not Ang-1, produced by the predominant primary tumors, which is stable and has a long half-life (data not shown), could travel to the distant organs and change the balance in favor of inhibiting tumor angiogenesis, which may contribute to the dormancy observed in some secondary tumors.

The ECM Association of Ang-1 Provides a Different Regulatory Mechanism for the Availability of Ang-1—Ang-1 is wildly expressed both in embryo and in adult and exhibits a more uniform expression pattern compared with that of Ang-2. Ang-2 has a wild expression pattern in embryo. However, in adult tissues, its expression is restricted in the tissues where vascular remodeling is ongoing, such as ovary, uterus, and placenta. Ang-2 is up-regulated by hypoxia and several different cytokines including VEGF and tumor necrosis factor, whereas the expression of Ang-1 is not affected.

The association of Ang-1 with the ECM reported herein offered a different type of regulation of the availability of Ang-1. Instead of regulating its production, as Ang-2, free Ang-1 in microenvironment can be regulated by changing its ECM association status. The factors that promote or inhibit its ECM incorporation or releasing affect the interaction between Ang-1 and Tie-2 receptor, sequential signal transduction, and angiogenesis. This type of regulation provides a quicker response to the changes in the microenvironment without the requirement of mRNA and proteins syntheses. It is well established that the activities of some growth factors are regulated in that way, including TGF.

The Biochemical Characters of the ECM Association of Ang-1—An extensive effort was made to try to identify the ECM component(s) that mediate(s) the ECM association of Ang-1. Matrigel, fibrinogen, and to a less extent vitronectin exhibited weak affinities to Ang-1, which is much lower than that of unpurified ECM extracts derived from LLC cells and cannot account entirely for the ECM association of Ang-1 (FIG. 4). The immunocytochemistry studies indicated that the ECM distribution pattern of Ang-1 is unique and unlike that of fibronectin, laminin, and collagen types I and IV (FIG. 5).

To determine the effect of the ECM association on the function of Ang-1, we assessed whether Tie-2-Fc fusion protein binds to the ECM-associated Ang-1. The result indicated that the ECM-associated Ang-1 is not accessible for Tie-2, and the ECM serves as a storage and sequestration site for Ang-1. The incubation of HUVECs on the ECM containing Ang-1 induced the release of Ang-1 from the ECM and tyrosine phosphorylation of Tie-2, which indicated that HUVECs cells are able to respond to Ang-1 originally sequestered in the ECM (FIG. 8). This may reflect the in vivo situations and indicate that activity of Ang-1 is restricted in local environment and regulated more tightly than that of Ang-2.

The Domain of Ang-1 That Mediates Its ECM Association Is the Linker Peptide Region—The deletion analysis indicated that the linker peptide region of Ang-1 between the coiled-coil domain and the FHD mediates the ECM association of Ang-1 (FIG. 9). The identification of the ECM association domain of Ang-1 will allow us to study the importance of the ECM association on Ang-1 function in the future.

In summary, we have discovered that Ang-1 is incorporated into the ECM after its secretion, whereas Ang-2 is secreted and does not associate with the ECM. The domain that mediates the ECM association of Ang-1 is mapped to the linker peptide region between the coiled-coil and the fibrinogen homology domains. The different ECM association capacity of Ang-1 and Ang-2 offers a possible mechanism for the distinct regulations of local and distant tumor angiogenesis by two antagonistic factors.

Abbreviations

The abbreviations used are: ECM, extracellular matrix; Ang-1, angiopoietin-1; Ang-2, angiopoietin-2; TA3, TA3 murine mammary carcinoma; LLC, Lewis lung carcinoma; HUVEC, human umbilical vein endothelial cell; FHD, fibrinogen homology domain; PBS, phosphate-buffered saline solution; BSA, bovine serum albumin; PCR, polymerase chain reaction; RT-PCR, reverse transcriptase-polymerase chain reaction; FITC, fluorescein isothiocyanate; DOC, deoxycholate; SFM, serum-free medium; PMA, phorbol 12-myristate 13-acetate; bFGF, basic fibroblast growth factor; TGF-, transforming growth factor-; VEGF, vascular endothelial growth factor.

REFERENCES

Which are Each Incorporated Herein by Reference

1. Folkman, J. (1971) N. Engl. J. Med. 285, 1182-1186
2. Kim, K. J., Li, B., Winer, J., Armanini, M., Gillett, N., Philips, H. S., and Ferrara, N. (1993) Nature 362, 841-844
3. Millauer, B., Shawver, L. K., Plate, K. H., Risau, W., and Ullrich, A. (1994) Nature 367, 576-579
4. Hanahan, D., and Folkman, J. (1996) Cell 86, 353-364
5. Risau, W. (1997) Nature 386, 671-674
6. Ingber, D. E., and Folkman, J. (1989) Cell 58, 803-805
7. Dumont, D. J., Grawohl, G., Fong, G. H., Puri, M. C., Gertsenstein, M., Auerbach, A., and Breitman, M. L. (1994) Genes Dev. 8, 1897-1909-[Abstract]
8. Mustonen, T., and Alitalo, K. (1999) J. Cell Biol. 129, 895-898
9. Fong, G. H., Rossant, J., Gertenstein, M., and Breitman, M. L. (1995) Nature 376, 66-70
10. Gale, N. W., and Yancopoulos, G. D. (1999) Genes Dev. 13, 1055-1066
11. Yancopoulos, G. D., Davis, S., Gale, N. W., Rudge, J. S., Wiegand, S. J., and Holash, J. (2000) Nature 407, 242-248
12. Hanahan, D. (1997) Science 277, 48-50
13. Davis, S., Aldrich, T. H., Jones, P. F., Acheson, A., Compton, D. L., Jain, V., Ryan, T. E., Bruno, J., Radziejewski, C., Maisonpierre, P., and Yancopoulos, G. D. (1996) Cell 87, 1161-1169
14. Maisonpierre, P. C., Suri, C., Jones, P. F., Bartunkova, S., Wiegand, S. J., Radziejewski, C., Compton, D., McClain, J., Aldrich, T. H., Papadopoulos, N., Daly, T. J., Davis, S., Sato, T. N., and Yancopoulos, G. D. (1997) Science 277, 55-60
15. Procopio, W. N., Pelavin, P. I., Lee, W. M. F., and Yeilding, N. M. (1999) J. Biol. Chem. 274, 30196-30201
16. Valenzuela, D. M., Griffiths, J. A., Rojas, J., Aldrich, T. H., Jones, P. F., Zhou, H., McClain, J., Copeland, N. G., Gilbert, D. J., Jenkins, N. A., Huang, T., Papadopoulos, N., Maisonpierre, P. C., Davis, S., and Yancopoulos, G. D. (1999) Proc. Natl. Acad. Sci. U.S.A. 96, 1904-1909

17. Yu, Q., and Stamenkovic, I. (2001) Am. J. Pathol. 158, 563-570
18. Suri, C., Jones, P. F., Patan, S., Bartunkova, S., Maisonpierre, P. C., Davis, S., Sato, T. N., and Yancopoulos, G. D. (1996) Cell 87, 1171-1180[
19. Sato, T. N., Tozawa, Y., Deutsch, U., Wolburg-Buchholz, K., Fujiwara, Y., Gendron-Magurire, M., Gridley, T., Wolbrug, H., Risau, W., and Qin, Y. (1995) Nature 376, 70-74
20. Suri, C., McClain, J., Thurston, G., McDonald, D. M., Zhou, H., Oldmixon, E. H., Sato, T. N., and Yancopoulos, G. D. (1998) Science 282, 468-471
21. Thurston, G., Suri, C., Smith, K., McClain, J., Sato, T. N., Yancopoulos, G. D., and McDonald, D. M. (1999) Science 286, 2511-2514
22. Thurston, G., Rudge, J. S., Ioffe, E., Zhou, H., Ross, L., Croll, S. D., Glazer, N., Holash, J., McDonald, D. M., and Yancopoulos, G. D. (2000) Nat. Med. 6, 460-463
23. Witzenbichler, B., Maisonpierre, P. C., Jones, P., Yancopoulos, G. D., and Isner, J. M. (1998) J. Biol. Chem. 273, 18514-18521
24. Koblizek, T. L., Weiss, C., Yancopoulos, G. D., Deutsch, U., and Risau, W. (1998) Curr. Biol. 8, 529-532
25. Hayes, A. J., Huang, W. Q., Mallah, J., Yang, D., Lippman, M. E., and Li, L. Y. (1999) Microvasc. Res. 58, 224-237
26. Papapetropoulos, A., Fulton, D., Mahboubi, K., Kalb, R. G., O'Connor, D. S., Li, F., Altieri, D. C., and Sessa, W. C. (2000) J. Biol. Chem. 275, 9102-9105
27. Kim, I., Kim, H. G., So, J. N., Kim, J. H., Kwak, H. J., and Koh, G. Y. (2000) Circ. Res. 86, 24-29
28. Kwak, H. J., Lee, S. J., Lee, Y. H., Ryu, C. H., Koh, K. N., Choi, H. Y., and Koh, G. Y. (2000) Circulation 101, 2317-2324
29. Stratmann, A., Risau, W., and Plate, K. H. (1998) Am. J. Pathol. 153, 1459-1466
30. Holash, J., Maisonpierre, P. C., Compton, D., Boland, P., Alexander, C. R., Zagzag, D., Yancopoulos, G. D., and Weigand, S. J. (1999) Science 284, 1994-1998
31. Oh, H., Takagi, H., Suzuma, K., Otani, A., Matsumura, M., and Honda, Y. (1999) J. Biol. Chem. 274, 15732-15739
32. Mandriota, S. J., and Pepper, M. S. (1998) Circ. Res. 83, 852-859
33. Kim, I., Kim, J. H., Ryu, Y. S., Liu, M., and Koh, G. Y. (2000) Biochem. Biophy. Res. Commun. 269, 361-365
34. Asahara, T., Chen, D., Takahashi, T., Fujikawa, K., Kearney, M., Magner, M., Yancopoulos, G. D., and Isner, J. M. (1998) Circ. Res. 83, 233-240
35. Holash, J., Wiegand, S. J., and Yancopoulos, G. D. (1999) Oncogene 18, 5356-5362
36. Lauren, J., Gunji, Y., and Alitalo, K. (1998) Am. J. Pathol. 153, 1333-1339
37. Yeo, T. K., Nagy, J. A., Yeo, K. T., Dvorak, H. F., and Toole, B. P. (1996) Am. J. Pathol. 148, 1733-1740
38. Kuno, K., and Matsushima, K. (1998) J. Biol. Chem. 273, 13912-13917
39. Massague, J. (1990) Annu. Rev. Cell Biol. 6, 597-641
40. Yu, Q., and Stamenkovic, I. (1999) Genes Dev. 13, 35-48
41. Ortega, N., L'Faqihi, F. E., and Plouct, J. (1998) Biol. Cell 90, 381-390
42. Klagsbrun, M. (1992) Semin. Cancer Biol. 3, 81-87
43. Fidler, I. J., and Ellis, L. M. (1994) Cell 79, 185-188
44. O'Reilly, M. S., Holmgren, L., Shing, Y., Chen, C., Rosenthal, R. A., Moses, M., Lane, W. S., Cao, Y., Sage, E. H., and Folkman, J. (1994) Cell 79, 315-328
45. Holmgren, L., O'Reilly, M. S., and Folkman, J. (1995) Nat. Med. 1, 149-153

---

The invention claimed is:

1. A pharmaceutical composition comprising
   a) a pharmaceutically acceptable carrier and
   b) a therapeutically effective amount of protein that consists of SEQ ID NO:1 or SEQ ID NO:2 for treating one of the following diseases: coronary artery disease, ischemia, and vascular diseases.

2. The pharmaceutical composition of claim 1 comprising a therapeutically effective amount of a protein that consists of SEQ ID NO:1.

3. The pharmaceutical composition of claim 1 comprising a therapeutically effective amount of a protein that consists of SEQ ID NO:2.

4. A method of treating an individual suspected of having coronary artery disease, vascular disease or a condition involving ischemia comprising the step of administering to said individual a pharmaceutical composition comprising
   a) a pharmaceutically acceptable carrier and
   b) therapeutically effective amount of protein that consists of SEQ ID NO:1 or SEQ ID NO:2.

5. The method of claim 4 wherein the protein consists of SEQ ID NO:1.

6. The method of claim 4 wherein the protein consists of SEQ ID NO:2.

7. A method of promoting angiogenesis, endothelial survival and maintaining vascular integrity in an individual comprising the step of administering to said individual a pharmaceutical composition comprising
   a) a pharmaceutically acceptable carrier and
   b) therapeutically effective amount of protein that consists of SEQ ID NO:1 or SEQ ID NO:2.

8. The method of claim 7 wherein the protein consists of SEQ ID NO: 1.

9. The method of claim 7 wherein the protein consists of SEQ ID NO:2.

10. A composition comprising a protein that consists of SEQ ID NO:1.

11. A composition comprising a protein that consists of SEQ ID NO:2.

* * * * *